(12) United States Patent
Lee et al.

(10) Patent No.: US 11,001,566 B2
(45) Date of Patent: May 11, 2021

(54) QUINAZOLINONE DERIVATIVE, PREPARATION METHOD THEREFOR, PHARMACEUTICAL COMPOSITION, AND APPLICATIONS

(71) Applicant: KANGPU BIOPHARMACEUTICALS, LTD, Shanghai (CN)

(72) Inventors: Wen-Cherng Lee, Shanghai (CN); Baisong Liao, Shanghai (CN)

(73) Assignee: Kangpu Biopharmaceuticals, Ltd., Shanghai (CN)

( * ) Notice: Subject to any disclaimer, the term of this patent is extended or adjusted under 35 U.S.C. 154(b) by 213 days.

(21) Appl. No.: 16/069,026

(22) PCT Filed: Jan. 13, 2017

(86) PCT No.: PCT/CN2017/071147
§ 371 (c)(1),
(2) Date: Jul. 10, 2018

(87) PCT Pub. No.: WO2017/121388
PCT Pub. Date: Jul. 20, 2017

(65) Prior Publication Data
US 2020/0039950 A1 Feb. 6, 2020

(30) Foreign Application Priority Data
Jan. 14, 2016 (CN) .......................... 201610023840.9

(51) Int. Cl.
C07D 401/04 (2006.01)
A61P 35/00 (2006.01)
A61K 45/06 (2006.01)
C07B 59/00 (2006.01)

(52) U.S. Cl.
CPC ............ C07D 401/04 (2013.01); A61P 35/00 (2018.01); A61K 45/06 (2013.01); C07B 59/002 (2013.01)

(58) Field of Classification Search
CPC ........................... C07D 401/04; A61K 31/517
USPC ..................................... 544/287; 514/266.21
See application file for complete search history.

(56) References Cited

U.S. PATENT DOCUMENTS

2015/0203469 A1  7/2015  Man et al.

FOREIGN PATENT DOCUMENTS

| CN | 104755472 A | 7/2015 |
| WO | 2008039489 A2 | 4/2008 |
| WO | 2009042177 A1 | 4/2009 |
| WO | 2012125475 A1 | 9/2012 |
| WO | 2014039421 A2 | 3/2014 |
| WO | 2014110558 A1 | 7/2014 |
| WO | 2014152833 A1 | 9/2014 |
| WO | 2016105518 A1 | 6/2016 |

OTHER PUBLICATIONS

Neuman, et. al., Drug and Discovery Today, vol. 8, No. 19, 2003.*
Chawla, et. al., CRIPS vol. 5, No. 1, 2004.*
Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Examination Report No. 1, Australian Patent Application No. 2017206382, dated Mar. 10, 2020.
Office Action, European Patent Office, Application No. 17 738 201.7-1110, dated Apr. 1, 2020.
Office Action, Russian Application No. 2018129344/04(047293), dated Feb. 20, 2020.
Search Report, Russian Application No. 2018129344/04(047293), dated Feb. 20, 2020.
Extended European Search Report dated Jun. 27, 2019 in EP Application No. 17738201.7.
Sethi et al, "TNF: A master switch for inflammation to cancer," Frontiers in Bioscience, pp. 5094-5107 (May 1, 2008).
Wajant, "The Role of TNF in Cancer," Death Receptors and Cognate Ligands in Cancer, pp. 1-15 (2009).
Stahl et al, "Handbook of Pharmaceutical Salts: Properties, Selection, and Use," pp. 329-350 (2002).
Rautio et al, "Prodrugs: design and clinical applications," Nature Reviews Drug Discovery, vol. 7, pp. 255-270 (2008).
Stella et al, "Prodrugs: Challenges and Rewards," Biotechnology: Pharmaceutical Aspects, vol. 10, Part 1 (2007).
Int'l Search Report dated Apr. 20, 2017 in Int'l Application No. PCT/CN2017/071147.

* cited by examiner

*Primary Examiner* — Jeffrey H Murray
(74) *Attorney, Agent, or Firm* — Ice Miller LLP

(57) ABSTRACT

Disclosed are a quinazolinone derivative, a preparation method therefor, a pharmaceutical composition, and applications. Provided are a compound represented by formula I, a pharmaceutically acceptable salt, a solvate, a crystal form, a eutectic crystal, a stereoisomer, an isotope compound, a metabolite, or a prodrug thereof. Generation or activity of a cell factor can be regulated, and accordingly, cancers and inflammatory diseases can be effectively treated.

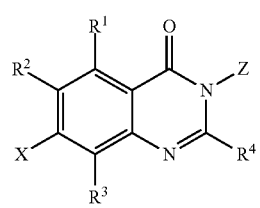

17 Claims, No Drawings

QUINAZOLINONE DERIVATIVE, PREPARATION METHOD THEREFOR, PHARMACEUTICAL COMPOSITION, AND APPLICATIONS

CROSS-REFERENCE TO RELATED APPLICATION

This application is a Section 371 of International Application No. PCT/CN2017/071147, filed Jan. 13, 2017, which was published in the Chinese language on Jul. 20, 2017, under International Publication No. WO 2017/121388 A1, which claims priority under 35 U.S.C. § 119(b) to Chinese Application No. 201610023840.9, filed Jan. 14, 2016, the disclosures of which are incorporated herein by reference in their entirety.

FIELD OF THE INVENTION

Provided are a quinazolinone derivative, a preparation process, a pharmaceutical composition and use thereof.

BACKGROUND OF THE INVENTION

Tumor necrosis factor-α (TNF-α) is a kind of proinflammatory cytokine, which plays an important role in immune homeostasis, inflammation, and host defense. TNF-α has been proved to be one of the major mediators of inflammation. TNF-α can also be produced by tumors. While being capable of promoting the formation of tumors, TNF-α can also cause the programmed death of tumor cells. In addition, TNF-α also affects the processes such as apoptosis, necrosis, angiogenesis, immune cell activation, differentiation and cell migration, all of which play important roles in tumorigenesis and tumor progression.

Uncontrolled activity of TNF-α or overproduction of TNF-α is associated with the pathology of various diseases, including but not limited to cancers, such as, colon, rectum, breast, brain and intestinal cancer; and inflammatory diseases, especially cancer-associated inflammation. The dysregulation of TNF-α can also lead to autoimmune diseases, toxic shock syndrome, cachexia, arthritis, psoriasis, HIV infection and AIDS, nervous system diseases and central nervous system diseases, sepsis, congestive heart failure, transplant rejection and virus infections. Thus, reducing the level of TNF-α, or regulating the activity of TNF-α is a promising strategy in treating many immunological, inflammatory and malignant diseases (e.g., cancers and inflammation). Such as, Sethi et al. *Front. Biosci.* (2008) 13, 5094-5107 and *Results Prob. Cell Differ.* (2009) 49, 1-15.

Lenalidomide (3-(4-amino-1,3-dihydro-1-oxo-2H-isoindol-2-yl)-piperidine-2,6-dione) is a small molecule immune regulator. It has been proved that lenalidomide can inhibit the secretion of TNF-α and other proinflammatory cytokines, and increase the secretion of anti-inflammatory cytokines. Lenalidomide was approved for treating multiple myeloma (in 2006), myelodysplastic syndrome (in 2005) and mantle cell lymphoma (in 2013). In addition, in clinical trials, Lenalidomide alone or in combination with other therapeutic agents, can treat non-Hodgkin's lymphoma, papillary and follicular thyroid carcinoma, chronic lymphocytic leukemia, chronic myelogenous leukemia, amyloidosis, type I complex regional pain syndrome, malignant melanoma, radiculopathy, myelofibrosis, glioblastoma, gliosarcoma, malignant glioma, myeloid leukemia, refractory plasma cell tumor, chronic myelomonocytic leukemia, follicular lymphoma, ciliary body and chronic melanoma, iridic melanoma, recurrent interocular melanoma, extraocular spreading melanoma, solid tumor, T cell lymphoma, erythroid lymphoma, monoblastic and monocytic leukemia; myeloid leukemia and brain tumors, meningioma, spinal tumor, thyroid cancer, mantle cell lymphoma, non-small cell lung cancer, ovarian cancer, renal cell carcinoma, Burkitt's lymphoma, Hodgkin's lymphoma, large cell lymphoma and macroglobulinemia (see WO 2012/015986).

However, Lenalidomide has many side effects. In fact, Lenalidomide's prescription information clearly recites that the drug has a risk of myelosuppression, deep vein thrombosis, pulmonary embolism and teratogenesis. During the clinical trials, a majority of patients taking Lenalidomide need a reduction of dose due to the hematologic toxicity. Therefore, although Lenalidomide is of useful activity, its effectiveness is limited by the significant occurrence of side effects. Therefore, it is desirable in the field to have Lenalidomide derivatives with improved structures to optimize its performance.

DISCLOSURE OF THE INVENTION

Provided are a quinazolinone derivative, a preparation process, a pharmaceutical composition and use thereof. The quinazolinone derivative of the invention can regulate generation or activity of cytokines such as TNF-α, thereby effectively treating cancer and inflammatory disease.

In an aspect of the invention, provided is a compound of Formula I, or a pharmaceutically acceptable salt, solvate, polymorph, co-crystal, stereoisomer, isotopic compound, metabolite, or prodrug thereof

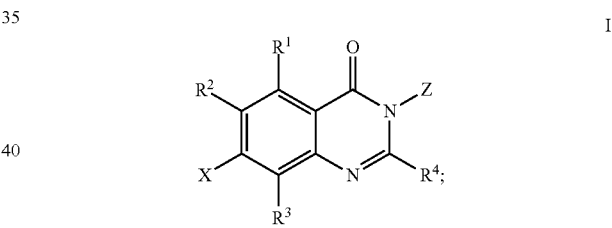

wherein,

X is selected from the group consisting of halogen, hydroxyl, cyano, substituted or unsubstituted $C_1$-$C_6$ alkyl, and $C_1$-$C_6$ alkoxy substituted with 6-10 membered aryl; wherein "6-10 membered aryl" in the "$C_1$-$C_6$ alkoxy substituted with 6-10 membered aryl" is optionally substituted with one or more of the following groups: D, halogen, hydroxyl, cyano, substituted or unsubstituted $C_1$-$C_6$ alkyl, and substituted or unsubstituted $C_1$-$C_6$ alkoxy, wherein when more than one substituents are present, they are identical or different;

Z is

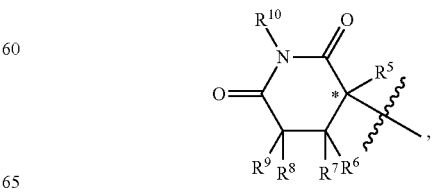

wherein the carbon marked with * is asymmetric center;
$R^1$ is selected from the group consisting of hydroxyl, substituted or unsubstituted $C_1$-$C_6$ alkoxy and —$NR^{1'}R^{2'}$; wherein $R^{1'}$ and $R^{2'}$ are each independently selected from the group consisting of H, D, substituted or unsubstituted $C_1$-$C_6$ alkyl and —$C(O)R^{3'}$; $R^{3'}$ is substituted or unsubstituted $C_1$-$C_6$ alkyl;
$R^2$, $R^3$, $R^5$, $R^6$, $R^7$, $R^8$, $R^9$, and $R^{10}$ are each independently H or D;
$R^4$ is $CH_3$, $CH_2D$, $CHD_2$ or $CD_3$;
the "substituted" in the above "substituted or unsubstituted $C_1$-$C_6$ alkoxy" and "substituted or unsubstituted $C_1$-$C_6$ alkyl" independently represents substitution with one or more of the following groups: D, halogen, amino, hydroxyl, cyano, $C_1$-$C_6$ alkoxy, and 4-10 membered heterocycloalkyl, wherein when more than one substituents are present, they are identical or different.

In an embodiment of the invention, the asymmetric center is preferably S configured carbon atom, enriched S configured carbon atom, R configured carbon atom, enriched R configured carbon atom or racemic carbon atom.

In an embodiment of the invention, the "halogen" in X is preferably fluorine, chlorine, bromine or iodine, more preferably fluorine, chlorine or bromine.

In an embodiment of the invention, when the "6-10 membered aryl" is optionally substituted with halogen, the "halogen" is preferably fluorine, chlorine, bromine or iodine, more preferably fluorine, chlorine or bromine.

In an embodiment of the invention, when the term "substituted" in "substituted or unsubstituted $C_1$-$C_6$ alkoxy" and "substituted or unsubstituted $C_1$-$C_6$ alkyl" independently refers to substitution with "halogen", the "halogen" is preferably fluorine, chlorine, bromine or iodine, more preferably fluorine, chlorine or bromine.

In an embodiment of the invention, the "$C_1$-$C_6$ alkyl" in "substituted or unsubstituted $C_1$-$C_6$ alkyl" is preferably "$C_1$-$C_4$ alkyl". The "$C_1$-$C_4$ alkyl" is preferably methyl, ethyl, isopropyl, n-propyl, n-butyl, isobutyl or tert-butyl, more preferably methyl or ethyl.

In an embodiment of the invention, the "$C_1$-$C_6$ alkoxy" in "substituted or unsubstituted $C_1$-$C_6$ alkoxy" is preferably "$C_1$-$C_4$ alkoxy". The "$C_1$-$C_4$ alkoxy" is preferably methoxy, ethoxy, isopropoxy, n-propoxy, n-butoxy, isobutoxy, tert-butoxy, n-pentyloxy or n-hexyloxy, more preferably methoxy.

In an embodiment of the invention, the "4-10 membered heterocycloalkyl" is preferably "5-6 membered heterocycloalkyl, wherein the heteroatom is one or more selected from the group consisting of N, O and S, and wherein the number of heteroatom is 1 or 2" (e.g., pyrrolidinyl, piperidinyl, piperazinyl, or morpholinyl), most preferably

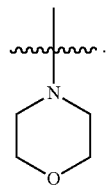

In an embodiment of the invention, the "$C_1$-$C_6$ alkoxy substituted with 6-10 membered aryl" is preferably a $C_1$-$C_4$ alkoxy substituted with phenyl; wherein the phenyl is optionally substituted with one or more of the following groups: D, halogen, hydroxyl, cyano, and $C_1$-$C_4$ alkyl sub-stituted with 4-10 membered heterocycloalkyl (e.g., $C_1$-$C_4$ alkyl substituted with pyrrolidinyl, piperidinyl, piperazinyl, or morpholinyl); more preferably selected from methoxy substituted with phenyl, wherein the phenyl is optionally substituted with one or more of the following groups: D, halogen, hydroxyl, cyano and $C_1$-$C_4$ alkyl substituted with morpholinyl, wherein when more than one substituents are present, they are identical or different.

In an embodiment of the invention, Z is selected from any of the following structures:

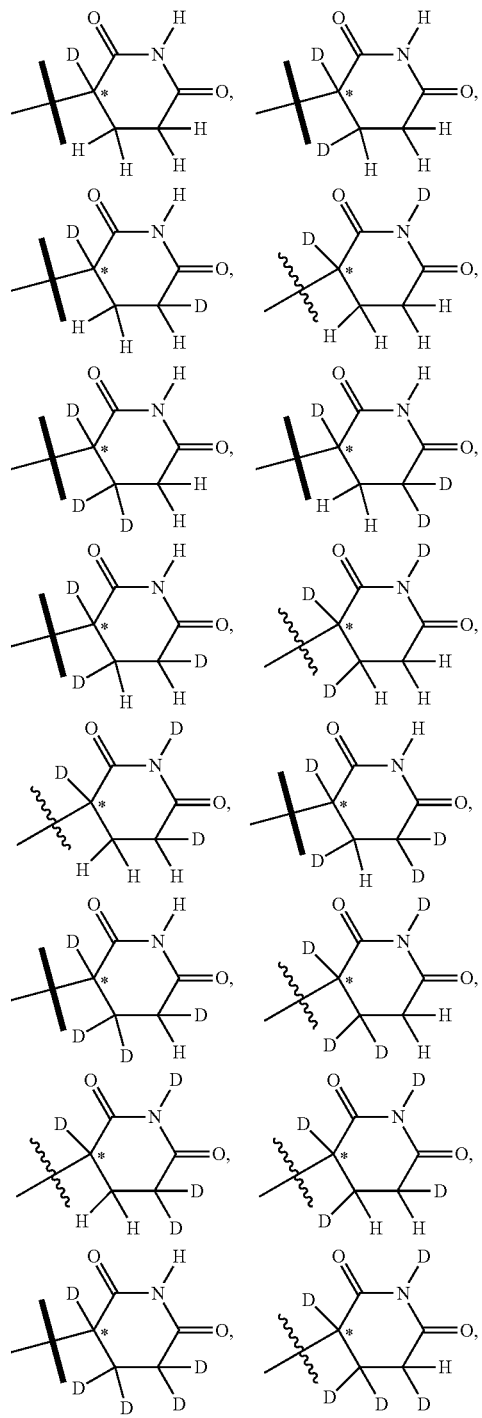

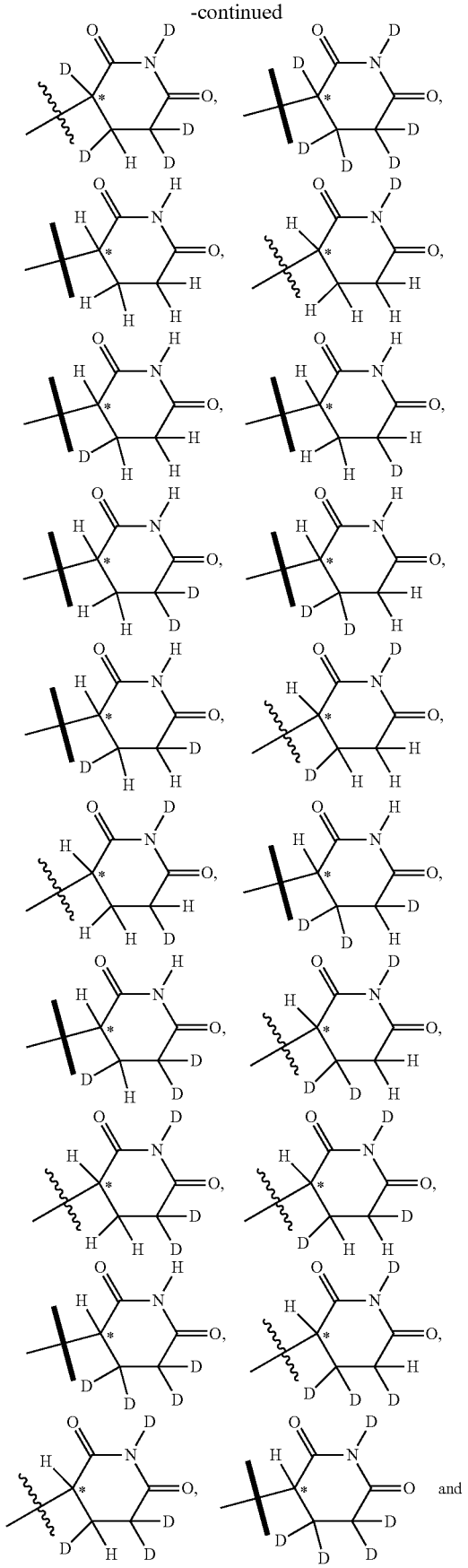

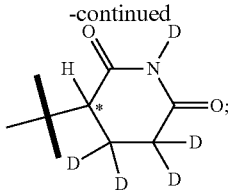

Z is preferably

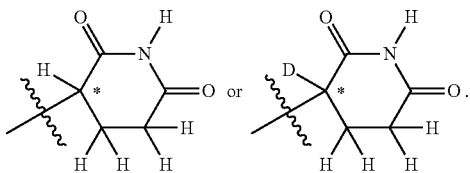 [SMILES: *C1CCC(=O)NC1=O ; *C1([2H])CCC(=O)NC1=O]

In an embodiment of the invention, $R^1$ is —$NR^{1'}R^{2'}$.

In an embodiment of the invention, $R^{1'}$ and $R^{2'}$ are each independently selected from the group consisting of H, D, substituted or unsubstituted $C_1$-$C_4$ alkyl, and —C(O)$R^{3'}$.

In an embodiment of the invention, $R^{3'}$ is a substituted or unsubstituted $C_1$-$C_4$ alkyl.

In an embodiment of the invention, $R^{3'}$ is selected from the group consisting of methyl, ethyl and isopropyl.

In an embodiment of the invention, $R^{1'}$ and $R^{2'}$ are each independently selected from the group consisting of H, D, methyl, ethyl, isopropyl, acetyl, propionyl and isobutyryl.

In an embodiment of the invention, X is selected from the group consisting of halogen, hydroxyl, cyano, substituted or unsubstituted $C_1$-$C_4$ alkyl, and methoxy substituted with phenyl; wherein the phenyl is optionally substituted with one or more of the following groups: D, halogen, hydroxyl, cyano, and $C_1$-$C_4$ alkyl substituted with morpholinyl, wherein when more than one substituents are present, they are identical or different.

In an embodiment of the invention, X is selected from the group consisting of fluorine, chlorine, bromine, hydroxyl, cyano, benzyloxy, 2-fluoro-4-(morpholinyl-1-methyl)benzyloxy, methyl, ethyl, $CD_3$, $C_2D_5$ and $CH_2CD_3$.

In an embodiment of the invention, X is halogen, $R^1$ is $NH_2$, NHD or $ND_2$; $R^2$, $R^3$, $R^5$, $R^6$, $R^7$, $R^8$, $R^9$ and $R^{10}$ are independently H or D; $R^4$ is $CH_3$, $CH_2D$, $CHD_2$ or $CD_3$.

Preferably, the compound of formula I is selected from any of the following structures:

K101

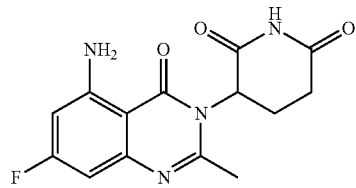

K102

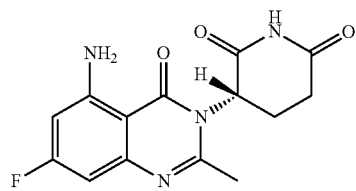

K103 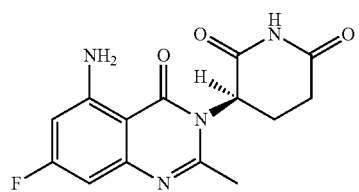
K104 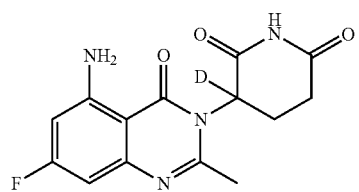
K105 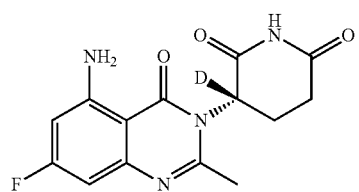
K106 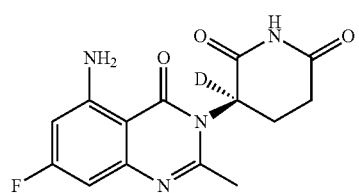
K113 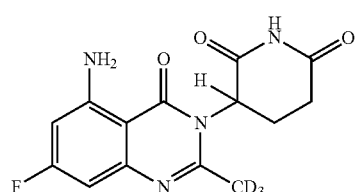
K116 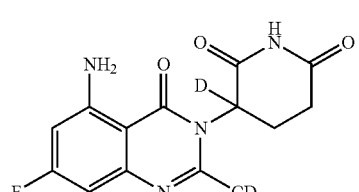
K113-1 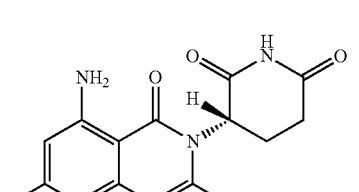
K118-1 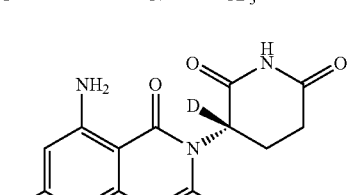
K401 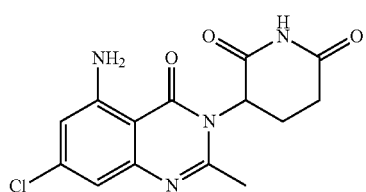
K402 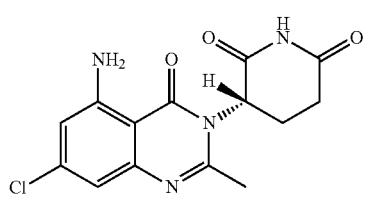
K403 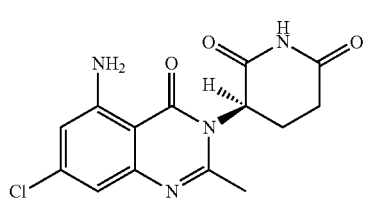
K404 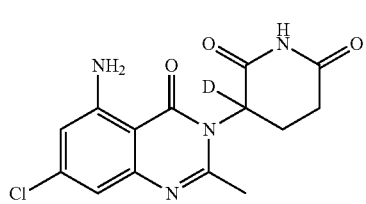
K405 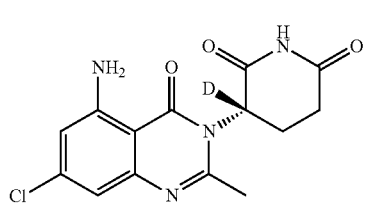
K406 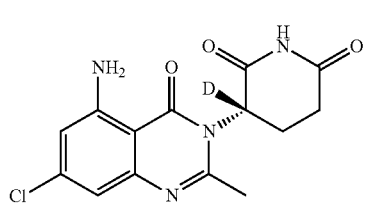
K409 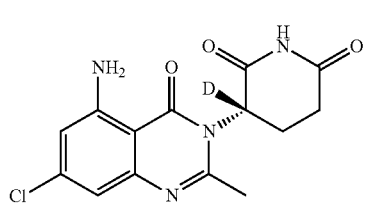
K409-1 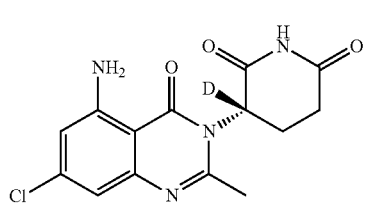

K410
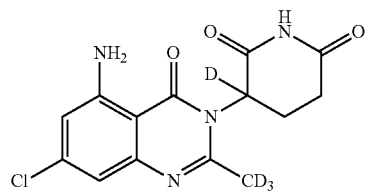
K410-1
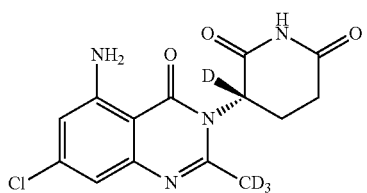
K431
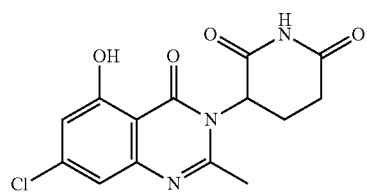
K431-1
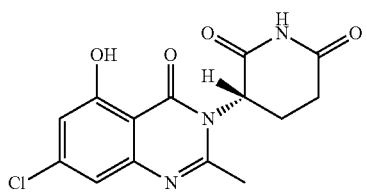
K432
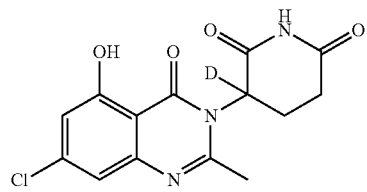
K432-1
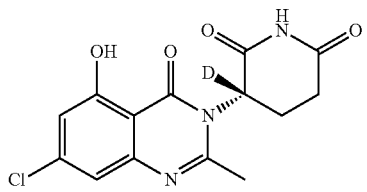
K501
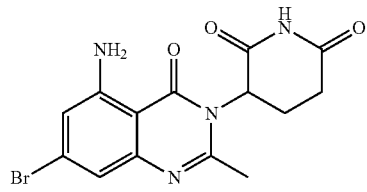
K502
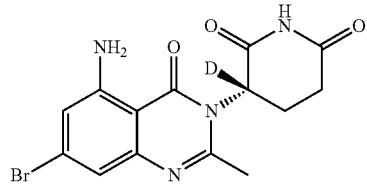
K503
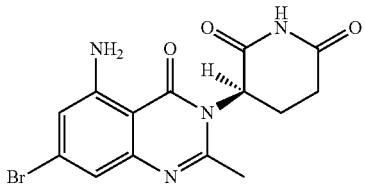
K504
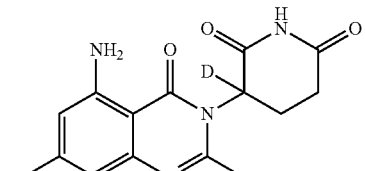
K505
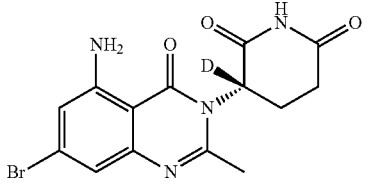
K506
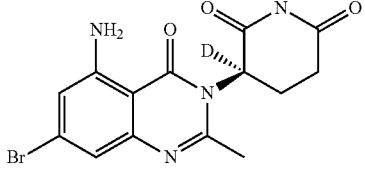
K509
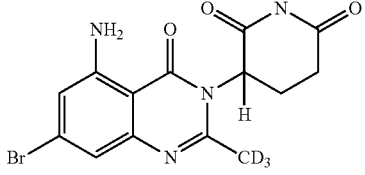
K509-1
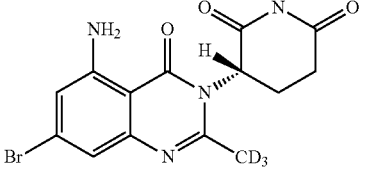
K510
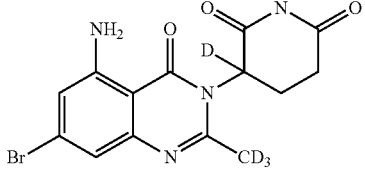
K510-1
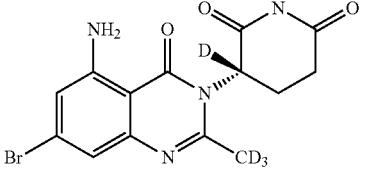

K531 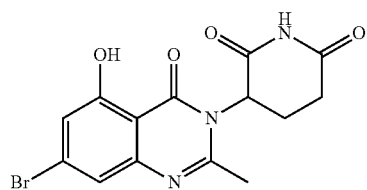
K531-1 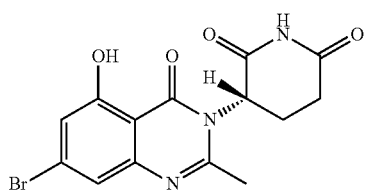
K532 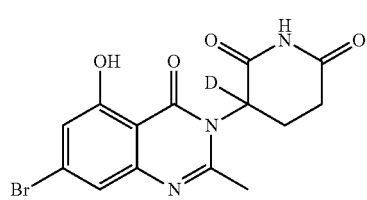
K532-1 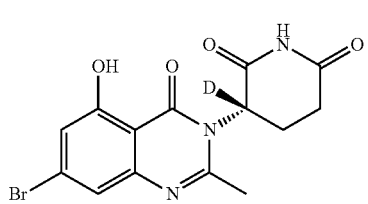
K613 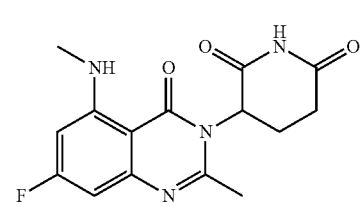
K613-1 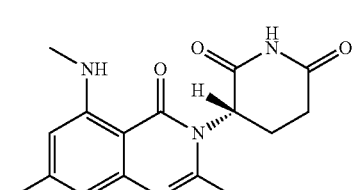
K614 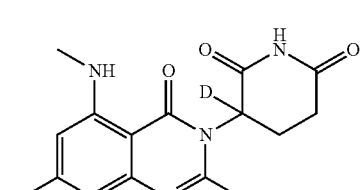
K614-1 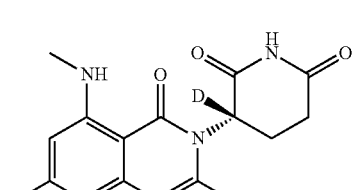
K615 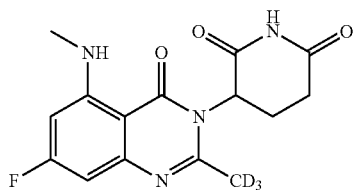
K615-1 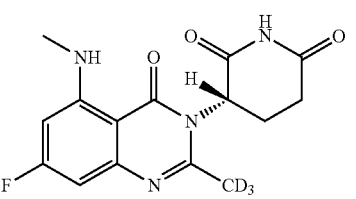
K616 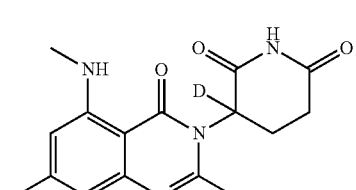
K615-1 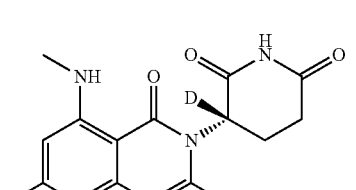
K617 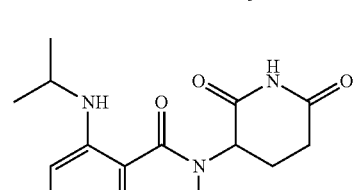
K617-1 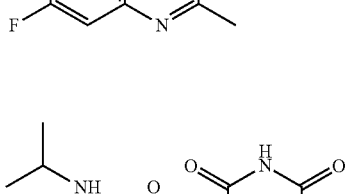
K620 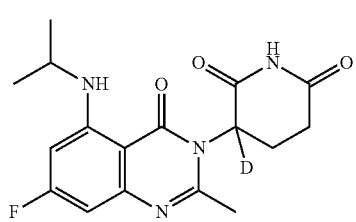

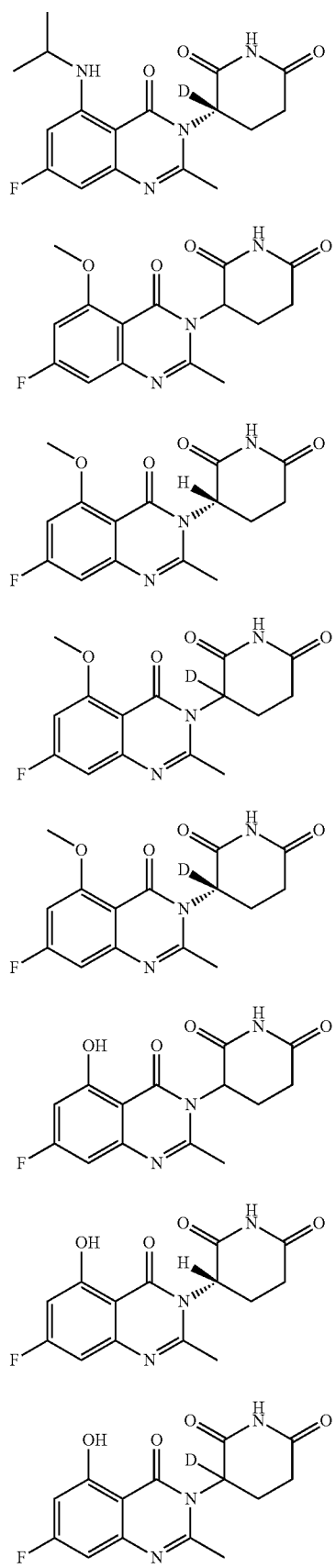
K620-1
K627
K627-1
K628
K628-1
K631
K631-1
K632
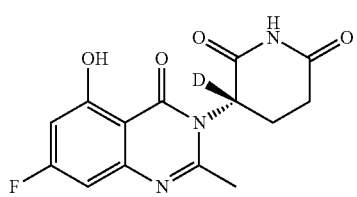
K632-1
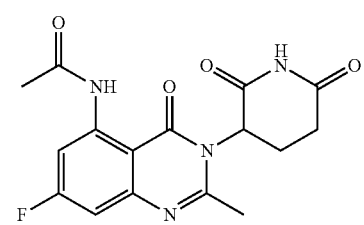
K633
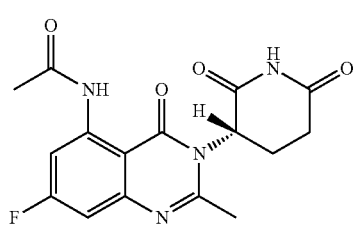
K633-1
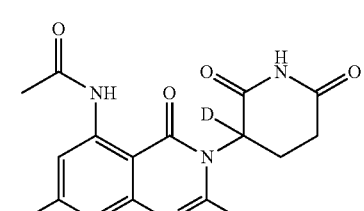
K634
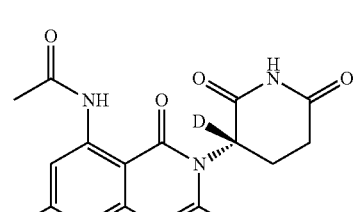
K634-1
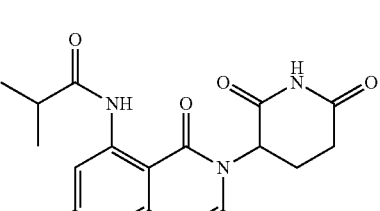
K635
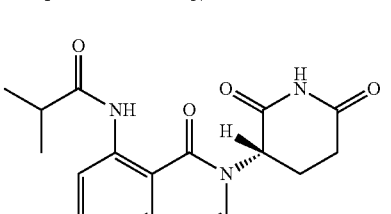
K635-1

-continued

K636

K636-1

K700

K700-1

K701

K700-1

K704

-continued

K704-1

K705

K705-1

K706

K706-1

K707

K707-1
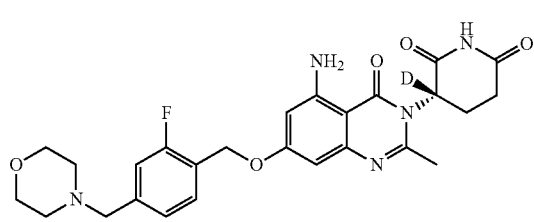
K720
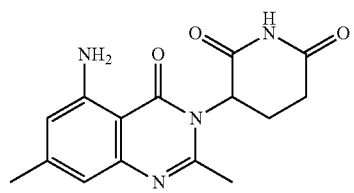
K720-1
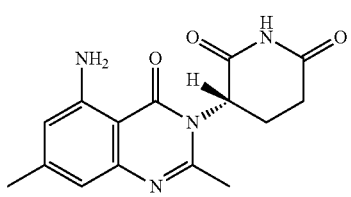
K720-2
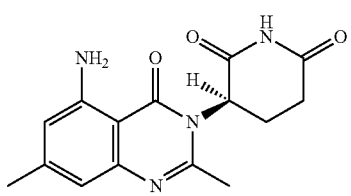
K721
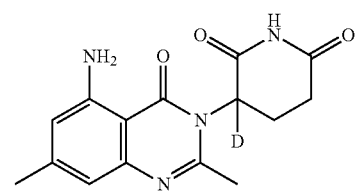
K721-1
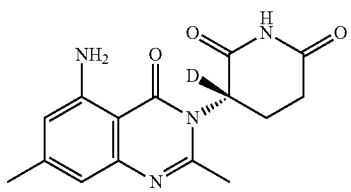
K721-2
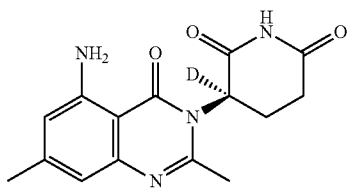
K728
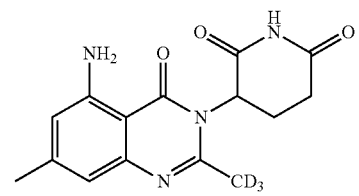
K728-1
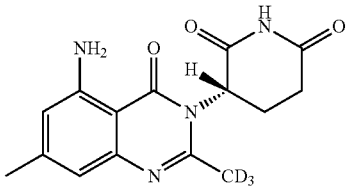
K729
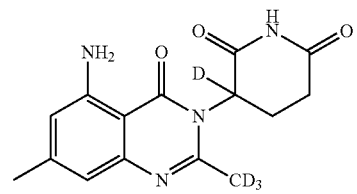
K729-1
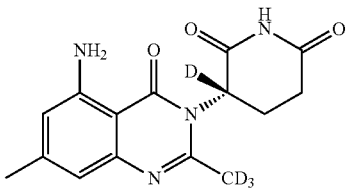
K722
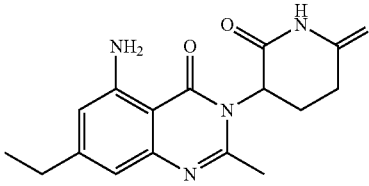
K722-1
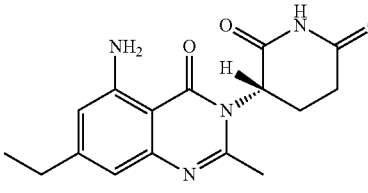
K723
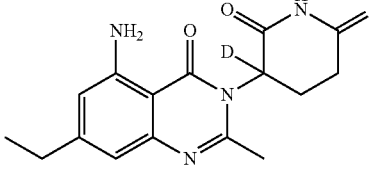
K723-1
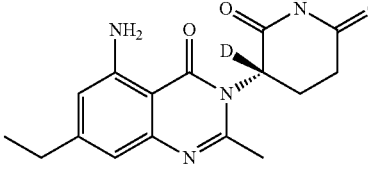
K724

K724-1 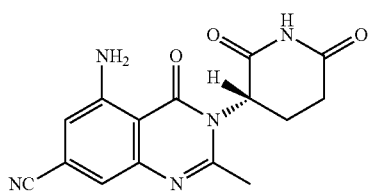

K724-2 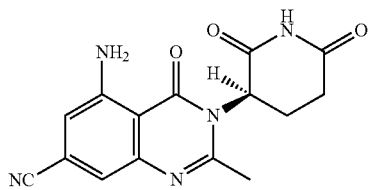

K725 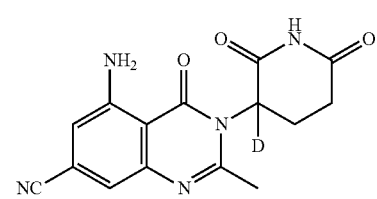

K725-1 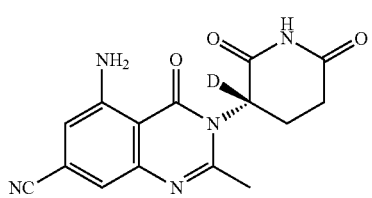

K725-2 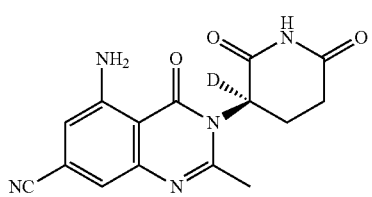

K730 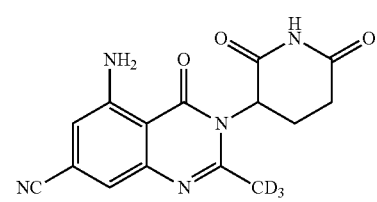

K730-1 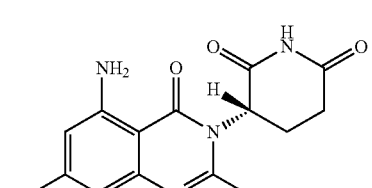

K731 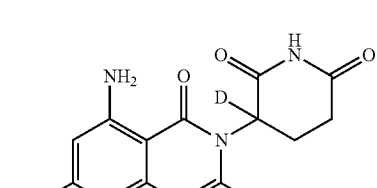

K731-1 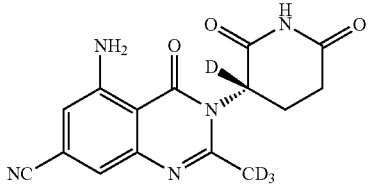

K726 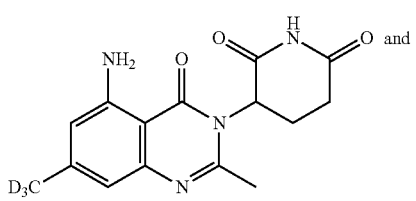

K727 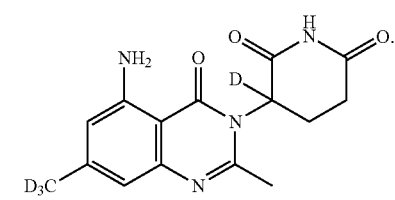

Provided is also a process for preparing the compound of formula I, which can be synthesized by known processes using commercially available starting materials. The invention gives particular preference to any one of the following.

Process A comprises the following step:

reducing or deprotecting compound A1 to give the compound of Formula I;

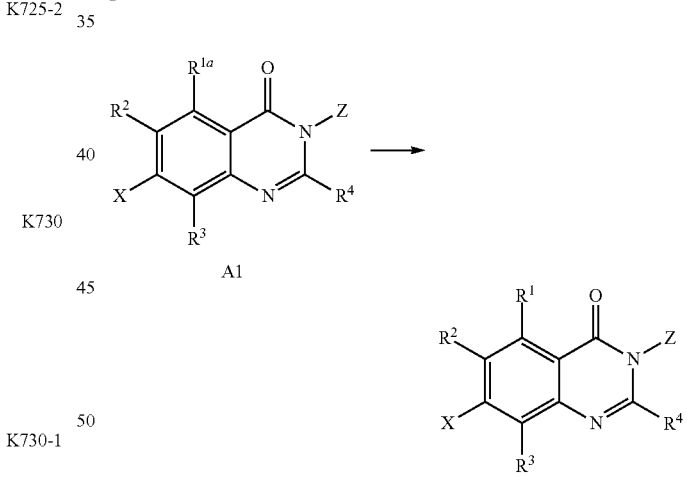

wherein $R^{1a}$ is nitro, azide or

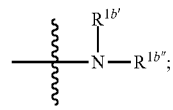

$R^{1b'}$ and $R^{1b''}$ are independently H, D or amino protecting group, provided that $R^{1b'}$ and $R^{1b''}$ are not simultaneously H or D. The definitions of $R^1$, $R^2$, $R^3$, $R^4$, X and Z are as defined above.

The amino protecting group may be an amino protecting group commonly used in the art, non-limiting examples being benzyloxycarbonyl (Cbz), tert-butoxycarbonyl (Boc), fluorenylmethyloxycarbonyl (Fmoc), p-methoxybenzyl (PMB), benzyl (Bn), etc.

Process B-1 comprises the following steps:

deprotecting compound B3 to give compound B2; and then subjecting compound B2 to amidation to give the compound of formula I;

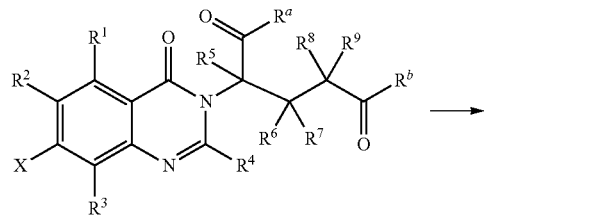

B3

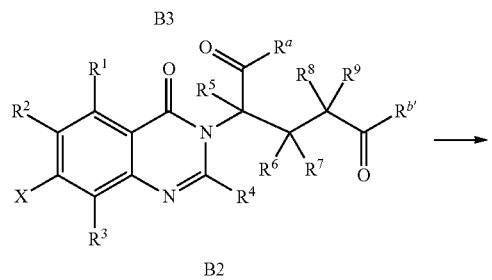

B2

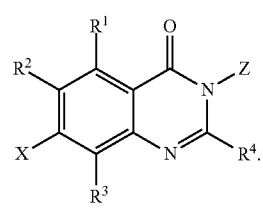

I

Process B-2 comprises the following steps:

subjecting compound B3 to cyclization reaction to give the compound of formula I;

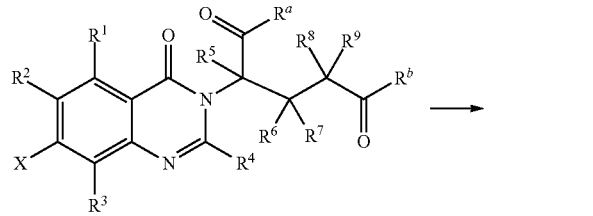

B3

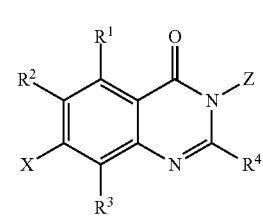

I

In Process B-1 and Process B-2, one of $R^a$ and $R^b$ is

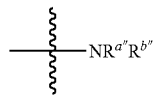

and the other is

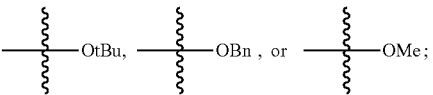

one of $R^{a'}$ and $R^{b'}$ is

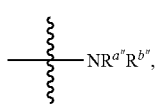

and the other is

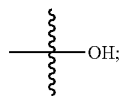

Ra" and Rb" are each independently H or D. The definitions of $R^1$, $R^2$, $R^3$, $R^4$, $R^5$, $R^6$, $R^7$, $R^8$, $R^9$, X and Z are as defined above.

Process C-1 comprises the following steps:

reacting compound C1 and compound Z—NH$_2$ as shown below to give the compound of Formula I;

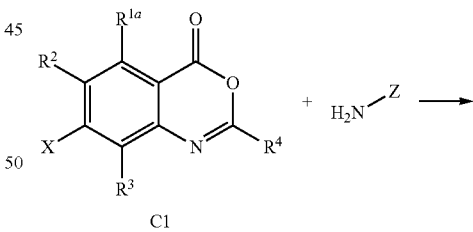

C1

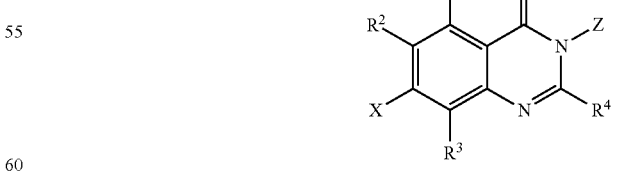

I wherein, the definitions of $R^1$, $R^2$, $R^3$, $R^4$, X and Z are as defined above.

Meanwhile, in Process C-1, Z group in compound Z—NH$_2$ may be replaced with

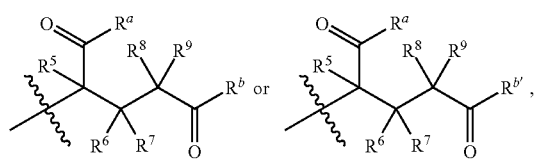

and/or $R^1$ group in compound C1 may be replaced with $R^{1a}$

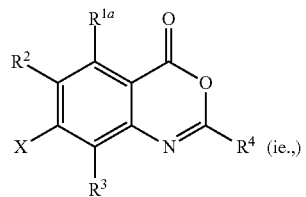

and the corresponding reactions are performed to give intermediate compound B3 or B2 or A1. Likewise, in Process A, Z group in compound A1 is replaced with

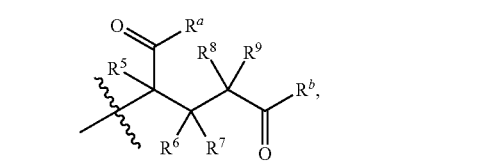

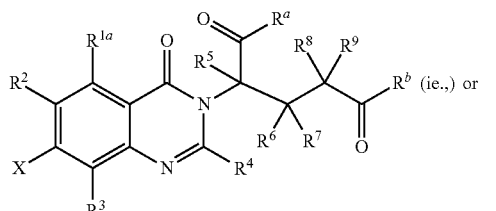

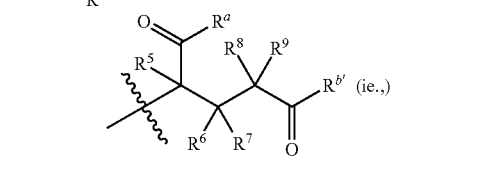

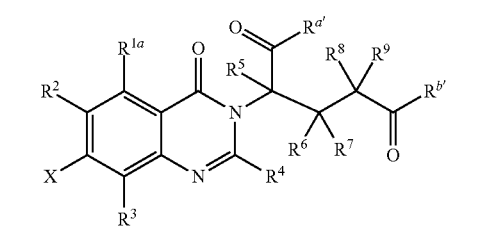

and the corresponding reaction are performed to give intermediate compound B3 or B2; wherein $R^{1a}$, $R^a$, $R^b$, $R^{a'}$, $R^{b'}$, $R^2$, $R^3$, $R^4$, $R^5$, $R^6$, $R^7$, $R^8$ and $R^9$, X and Z are as defined above.

The conditions and steps applied in the chemical reactions involved in the above processes can be performed by referring to the routine conditions and steps for this type of reaction in the art, and the compound obtained by the above process can be further modified on the peripheral positions to obtain other target compounds of the invention.

Provided is also an intermediate compound of Formulae A1, A1-1, A1-2, B2, B3, C1, C1-1:

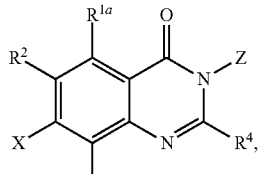

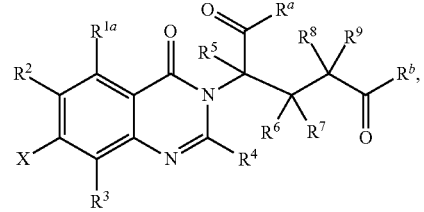

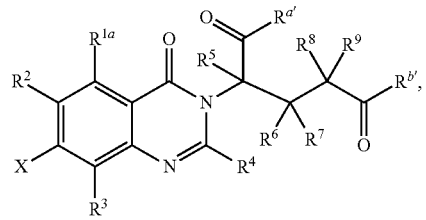

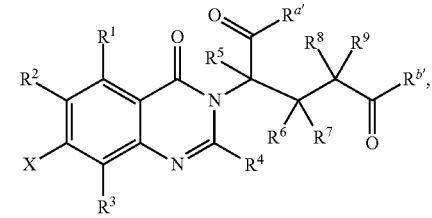

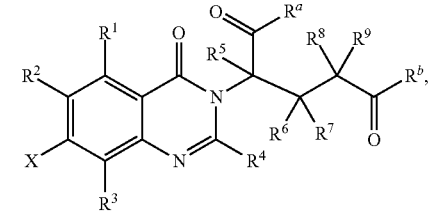

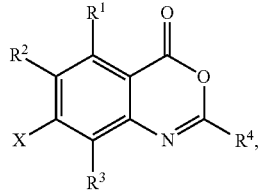

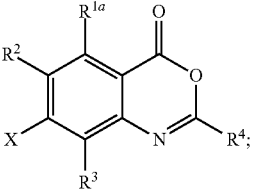

wherein $R^{1a}$, $R^a$, $R^b$, $R^{a'}$, $R^{b'}$, $R^1$, $R^2$, $R^3$, $R^4$, $R^5$, $R^6$, $R^7$, $R^8$, $R^9$, X and Z are as defined above.

Provided is also a pharmaceutical composition comprising the compound of formula I, or the pharmaceutically acceptable salt, solvate, polymorph, co-crystal, stereoisomer, isotopic compound, metabolite or prodrug thereof, and one or more pharmaceutically acceptable excipients.

The pharmaceutically acceptable excipient may be those widely used in drug manufacture. Excipients are mainly used to provide a safe, stable and functionalized pharmaceutical composition, and can also provide a method which makes the active ingredient dissolve at a desired rate or facilitates effective absorption of the active ingredient after being administered to a subject. The excipient can be an inert filler, or one that provides some functions, such as stabilizing the overall pH value of the composition or preventing the degradation of the active ingredient of the composition. The pharmaceutically acceptable excipient may comprise one or more excipients selected from the group consisting of binder, suspending agent, emulsifier, diluent, filler, granulating agent, adhesive, disintegrating agent, lubricant, anti-adhesive agent, glidant, wetting agent, gelling agent, absorption retarder, dissolution inhibitor or reinforcing agent, adsorbent, buffer, chelating agent, preservative, colorant, corrigent and sweetening agent.

The pharmaceutical composition of the invention can be prepared based on the contents disclosed herein according to any method known by one skilled in the art. For example, the pharmaceutical composition can be prepared by mixing the compound of formula I, or the pharmaceutically acceptable salt, solvate, polymorph, co-crystal, stereoisomer, isotopic compound, metabolite or prodrug thereof, with one or more pharmaceutically acceptable excipients, based on common preparation technology for medicaments. The technologies include but not limited to conventional mixing, dissolving, granulating, emulsifying, levigating, wrapping, embedding or freeze-dry process.

The pharmaceutical composition according to the invention may be formulated for administration in any route, including injection (intravenous), mucosal, oral administration (solid and liquid preparation), inhalation, ocular administration, rectal administration, topical or parenteral (infusion, injection, implantation, subcutaneous, vein, artery, intramuscular) administration. The pharmaceutical composition of the invention can also be controlled release or delayed release dosage forms. Examples of solid oral preparation include but not limited to powder, capsule, caplet, soft capsule or tablet. Examples of liquid preparation for oral or mucosal administration include but not limited to suspension, emulsion, elixir and solution. Examples of topical preparation include but not limited to emulsion, gel, ointment, cream, patch, paste, foam, lotion, drops or serum preparation. Examples of preparation for parenteral administration include but not limited to injection solution, dry preparation which can be dissolved or suspended in a pharmaceutically acceptable carrier, injectable suspension and injectable emulsion. Examples of other suitable preparations of the pharmaceutical composition include but not limited to eye drops and other ophthalmic preparations; aerosol, such as nasal spray or inhalation; liquid dosage forms suitable for parenteral administration; suppository and pastille.

The pharmaceutical composition of the invention may further comprise one or more other therapeutic agents. More information on the other therapeutic agents that may be comprised in the pharmaceutical composition of the invention is disclosed below. The amount and type of the other therapeutic agents depend on the disease, disorder or condition to be treated or prevented, the severity of disease, disorder or condition, and the factors of the subject to be administered with the composition, such as age, weight, physical condition, etc; and administration route, etc.

The therapeutic or prophylactic amount of the compound of formula I, or the pharmaceutically acceptable salt, solvate, polymorph, co-crystal, stereoisomer, isotopic compound, metabolite or prodrug thereof, any pharmaceutical composition or preparation thereof etc., may be administrated to a subject over a period (drug delivery cycle), followed by a period free of the compound (non-drug delivery cycle). The drug delivery cycle and non-drug delivery cycle can be repeated for required times. The required length and time of the drug delivery cycle and non-drug delivery cycle depend on the type and/or severity of the disease, disorder or condition being treated or prevented, and the gender, age, weight of the subject, and other parameters (e.g., the subject's biological, physical and physiological conditions, etc.). One skilled in the art can sufficiently determine a suitable length and time for the drug delivery cycle and non-drug delivery cycle based on the contents disclosed herein.

In another aspect of the invention, provided is a method for regulating the generation or activity of TNF-α, which comprises administering to a subject in need thereof a therapeutically effective amount of the compound of formula I, or the pharmaceutically acceptable salt, solvate, polymorph, co-crystal, stereoisomer, isotopic compound, metabolite or prodrug thereof, or the pharmaceutical composition thereof.

In another aspect of the invention, provided is use of the compound of formula I, or the pharmaceutically acceptable salt, solvate, polymorph, co-crystal, stereoisomer, isotopic compound, metabolite or prodrug thereof in the manufacture of a regulator for generation or activity of TNF-α.

In an embodiment, when the term "regulate" is used to describe the activity or generation of a specific molecule, it refers to inhibiting the activity or generation of the molecule. In another embodiment, when the term "regulate" is used to describe the activity or generation of a specific molecule, it refers to increasing or enhancing the activity or generation of the molecule. However, in another embodiment, when the term "regulate" is used to describe the activity or generation of a specific molecule, it refers to decreasing or increasing the activity or generation of the molecule.

Provided is use of the compound of formula I, or the pharmaceutically acceptable salt, solvate, stereoisomer, isotopic compound, metabolite or prodrug thereof in the manufacture of a medicament for treating or preventing a disease, disorder or condition. In another aspect, provided is a method for treating or preventing a disease, disorder or condition comprising administering to a subject a therapeutically or prophylactically effective amount of the compound of formula I, or the pharmaceutically acceptable salt, solvate, stereoisomer, isotopic compound, metabolite and prodrug thereof, or the pharmaceutical composition thereof. Examples of the disease, disorder or condition to be treated or prevented include but not limited to TNF-α associated disorders, cancers, diseases and disorders associated with undesired angiogenesis, pains, macular degeneration (MD) syndrome, skin diseases, keratosis, respiratory system disease (such as pulmonary diseases), immunodeficiency diseases, central nervous system (CNS) diseases, autoimmune diseases, atherosclerosis, heredity, allergy, viruses, sleep disorders and associated syndrome, inflammatory diseases, PDE-4 associated diseases or IL-2 associated diseases. Well-known examples of the disease, disorder or condition in the field include but not limited to those described in PCT patent publications WO2012015986 and WO2006018182 and US patent publication US20100204227.

Examples of TNF-α associated disease of the invention include but are not limited to, those diseases or disorders described in WO9803502. Specific examples include but are not limited to inflammation; cancers; endotoxemia or toxic shock syndrome; cachexia; adult respiratory distress syndrome; bone resorption diseases such as arthritis; hypercalcemia; graft-versus-host reaction; brain type disease; chronic pulmonary inflammatory disease; reperfusion injury; myocardial infarction; stroke; circulatory shock; rheumatoid arthritis; Crohn's disease; HIV infection and AIDS; other diseases such as rheumatoid spondylitis, osteoarthritis, psoriatic arthritis, septic shock, sepsis, wasting disease, ulcerative colitis, multiple sclerosis, systemic lupus erythematosus; asthma; autoimmune diseases; radiation damage; hyperoxic alveoli injury; viral infections such as those caused by the herpes virus; viral conjunctivitis or atopic dermatitis.

In a preferred embodiment, the TNF-α associated disease, disorder or condition of the invention is selected from myelodysplastic syndrome, multiple myeloma, mantle cell lymphoma, diffuse large B cell lymphoma, central nervous system lymphoma, non-Hodgkin's lymphoma; papillary and follicular thyroid carcinoma; breast cancer, chronic lymphocytic leukemia, chronic myelogenous leukemia, amyloidosis, type I complex regional pain syndrome, malignant melanoma, radiculopathy, myelofibrosis, glioblastoma, gliosarcoma, malignant glioma, refractory plasma cell tumor, chronic myelomonocytic leukemia, follicular lymphoma, ciliary body and chronic melanoma, iridic melanoma, recurrent interocular melanoma, extraocular extension melanoma, solid tumor, T-cell lymphoma, erythroid lymphoma, monoblastic and monocytic leukemia; myeloid leukemia, brain tumor, meningioma, spinal tumor, thyroid cancer, non-small cell lung cancer, ovarian cancer, renal cell carcinoma, Burkitt's lymphoma, Hodgkin's lymphoma, large cell lymphoma, astrocytoma, hepatocellular carcinoma, primary macroglobulinemia (Waldenstrom macroglobulinemia). In an embodiment, the cancer is metastatic. In another embodiment, the cancer is refractory or ineffective with the treatment of chemotherapy or radiation therapy.

The method for treating or preventing a disease, disorder or condition of the invention comprises administering the compound of formula I, or the pharmaceutically acceptable salt, solvate, stereoisomer, isotopic compound, metabolite and prodrug thereof to a subject by any suitable means, such as injection, mucosal, oral, inhalation, ocular, rectal, long-acting implant, liposome, emulsion or sustained release method.

One skilled in the art understands that the therapeutically effective or prophylactically effective amount of the compound used in the invention may vary with factors for a specific subject, such as age, diet, health, etc., the severity, complication and type of the disease, disorder or condition to be treated or prevented, and the preparation used etc. Based on the disclosures of the invention, one skilled in the art can easily determine therapeutically effective or prophylactically effective amount of the compound to be administered to the subject, so as to induce the desired biological or medical response in the subject.

In any method or application described in the invention, the compound of formula I, or the pharmaceutically acceptable salt, solvate, polymorph, co-crystal, stereoisomer, isotopic compound, metabolite or prodrug thereof, can be used alone or in combination with radiation therapy or radioimmunotherapy and the like, and may be used in further combination with one or more therapeutic agents having pharmaceutical activity (hereinafter referred to as "other therapeutic agent(s)")

In an embodiment of the invention, the other therapeutic agent(s) may be a natural, semisynthetic or synthetic compound. In another embodiment, the other therapeutic agent(s) may be a small molecule, such as a synthetic organic or inorganic molecule, or a larger molecule or biomolecule, such as proteins or nucleic acids with pharmacologically activity. In other embodiment, the other therapeutic agent(s) may be anti-angiogenic agent, immunoregulating agent, immunotherapeutic agent, chemotherapeutic agent or hormone compound.

In an embodiment of the invention, a composition comprising the compound of formula I, or the pharmaceutically acceptable salt, solvate, polymorph, co-crystal, stereoisomer, isotopic compound, metabolite or prodrug thereof, and another therapeutic agent is administrated to a subject simultaneously. In another embodiment, the compound of formula I, or the pharmaceutically acceptable salt, solvate, polymorph, co-crystal, stereoisomer, isotopic compound, metabolite or prodrug thereof, and the other therapeutic agent are administrated sequentially. In another embodiment, the compound of formula I, or the pharmaceutically acceptable salt, solvate, stereoisomer, isotopic compound, metabolite or prodrug thereof, and the other therapeutic agent are administrated separately. The other therapeutic agent can be administrated before, in succession to, or after the administration of the compound of formula I, or the pharmaceutically acceptable salt, solvate, polymorph, co-crystal, stereoisomer, isotopic compound, metabolite or prodrug thereof.

According to the invention, one or more other therapeutic agents, which can be administrated in combination with the compound of formula I, or the pharmaceutically acceptable salt, solvate, polymorph, co-crystal, stereoisomer, isotopic compound, metabolite or prodrug thereof, depend on a variety of factors, such as the disease, disorder or condition to be treated or prevented, etc. One skilled in the art can easily determine suitable other therapeutic agent(s) to be administrated in combination with the compound of formula I, or the pharmaceutically acceptable salt, solvate, polymorph, co-crystal, stereoisomer, isotopic compound, metabolite or prodrug thereof, based on the contents disclosed herein.

The therapeutically effective amount of the other therapeutic agent used in the method of the invention is known by one skilled in the art, and administration guidance can be referred to the patents and published applications cited herein, and Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000) and other medical literatures cited herein. However, one skilled in the art is capable of determining the optimal dose range of the other therapeutic agent.

According to an embodiment of the invention, when being administered in combination with other therapeutic agent(s), the therapeutically effective amount of the compound of formula I, or the pharmaceutically acceptable salt, solvate, polymorph, co-crystal, stereoisomer, isotopic compound, metabolite or prodrug thereof is less than the required therapeutically effective amount of the compound of formula I, or the pharmaceutically acceptable salt, solvate, polymorph, co-crystal, stereoisomer, isotopic compound, metabolite or prodrug thereof not in combination with other therapeutic agent(s). In another embodiment, the therapeutically effective amount of the other therapeutic agent(s) is less than that when the administration is performed without the compound of formula I, or the pharmaceutically acceptable salt, solvate, polymorph, co-crystal, stereoisomer, isotopic compound, metabolite or prodrug thereof. By this means, the side effects associated with high dose of any of the drugs can be minimized. Other potential advantages, for example, improving the administration regimen and/or lowering the cost of the drugs, are obvious to one skilled in the art.

According to an embodiment of the invention, when the compound of formula I, or the pharmaceutically acceptable salt, solvate, polymorph, co-crystal, stereoisomer, isotopic compound, metabolite or prodrug thereof, and the other therapeutic agent(s) are administered to a subject to treat or prevent a disease, disorder or condition, the compound of formula I, or the pharmaceutically acceptable salt, solvate, polymorph, co-crystal, stereoisomer, isotopic compound, metabolite or prodrug thereof, and the other therapeutic agent(s) can be administered in the same or different routes. The other therapeutic agent(s) can be administered in any ways described herein, including but not limited to, oral, inhalation, injection, ocular, mucosal, rectal, emulsion, liposome, long-acting implant or sustained release method. The specific administration route of the other therapeutic agent(s) depends on the agent itself and the preparation, and the disease, disorder or condition to be prevented or treated. According to the disclosures herein, one skilled in the art is capable of determining the administration route of the other therapeutic agent(s).

The present application cites or describes a variety of publications, articles and patents, the purpose of citing or describing these references or incorporating these references by their entireties or discussing these references is to illustrate the background of the invention rather than admission that the contents of these references contribute to a part of the prior art of the invention.

Unless otherwise defined, the technical and scientific terms used herein have the same meanings as those commonly understood by one skilled in the art. Otherwise, certain terms used herein have the meanings specified in the present description. All the patents, published applications and publications cited herein are incorporated herein by reference, just like elaborating in detail herein. It should be noted that, unless otherwise indicated explicitly in the context, the singular form used herein and in the attached claims encompass the plural meaning.

As used herein, when the specific salt, composition, and excipient etc. are referred to as "pharmaceutically acceptable", it means that the salt, composition, or excipient etc. are generally non-toxic, safe, and suitable for administration to a subject, preferably mammalian, more preferably human.

The term "pharmaceutically acceptable salt" used herein refers to a pharmaceutically acceptable organic or inorganic salt. Examples of the salt include but are not limited to, sulfate, citrate, acetate, oxalate, chloride, bromide, iodide, nitrate, hydrosulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzosulfonate, p-toluenesulfonate, and embonate (i.e. 1-1-methylene-bis(2-hydroxyl-3-naphthoate)). The compounds of the invention may be used to form pharmaceutically acceptable salts with various amino acids. Suitable alkali salt includes but is not limited to, aluminum salt, calcium salt, lithium salt, magnesium salt, potassium salt, sodium salt, zinc salt, bismuth salt and diethanolamine salt. Review regarding pharmaceutically acceptable salts is referred to Handbook of Pharmaceutical Salts: Properties, Selection, and Use (P. Heinrich Stahl and Camille G. Wermuth, ed., Wiley-VCH, 2002).

As used herein, the term "metabolite" refers to an active substance produced by a drug molecule which has gone through chemical structure changes in vivo, the active substance is generally a derivative of the aforementioned drug molecule, and also can be chemically modified.

As used herein and unless otherwise specified, the term "polymorph" refers to one or more kinds of crystal structure formed by different arrangements of molecules in the lattice space when crystallizing.

As used herein, the term "co-crystal" refers to a multi-component system comprising one or more API (active pharmaceutical ingredient) molecules and one or more object (or ligand) molecules. In the co-crystal, API molecules and object (or ligand) molecules exist as solids at room temperature when they are used in their pure form alone (in order to distinguish co-crystal from solvate or hydrate). From this particular definition, salts in which significant or complete proton exchange occurs between API molecules and guest molecules are excluded. In the co-crystal, API and ligands interact through hydrogen bonds and other possible non-covalent interactions. It is noted that the co-crystal itself may form solvates, including hydrates.

As used herein, the term "solvate" refers to a crystal form of the compound of formula I, or the pharmaceutically acceptable salt, polymorph, co-crystal, stereoisomer, isotopic compound, metabolite or prodrug thereof, which further has one or more solvent molecules incorporated into the crystal structure. The solvate may include a stoichiometric amount or a non-stoichiometric amount of solvent, and the solvent molecule in the solvent may exist in an ordered or non-ordered arrangement. The solvate containing a non-stoichiometric amount of solvent molecules may be formed by losing at least one solvent molecule (but not all) from the solvate. In a particular embodiment, a solvate refers to a hydrate, which means the crystal of the compound further includes water molecule, and water is used as a solvent.

As used herein and unless otherwise specified, the term "prodrug" refers to a derivative of the compound comprising a biologically reactive functional group, the biological reactive functional group can be cleaved from the compound or react in other ways to give the compound under biological conditions (in vivo or in vitro). Usually, the prodrug is inactive, or at least has lower activity than the compound, which makes the compound exhibit its activity after it is cleaved from the biologically reactive functional group. The biologically reactive functional group can be hydrolyzed or oxidized under biological conditions to give the compound. For instance, the prodrug may contain a biologically hydrolysable group. Examples of the biologically hydrolysable group include, but are not limited to, a biologically hydrolysable phosphate, a biologically hydrolysable ester, a biologically hydrolysable amide, a biologically hydrolysable carbonic ester, a biologically hydrolysable carbamate and a biologically hydrolysable ureide. Review regarding the prodrug refers to, such as J. Rautio et al., Nature Reviews Drug Discovery (2008) 7, 255-270 and Prodrugs: Challenges 和 Rewards (V. Stella et al. ed., Springer, 2007).

The compound of formula I in the invention, the pharmaceutically acceptable salt, solvate, polymorph, co-crystal, stereoisomer, isotopic compound, metabolite or prodrug thereof, can contain one or more asymmetric centers ("stereoisomer"). As used herein, the term "stereoisomer" refers to all stereoisomers including enantiomer, diastereoisomer, epimer, endo-exo isomer, atropisomer, regioisomer, cis- and trans-isomer. The "stereoisomer" herein also includes "pure stereoisomer" and "enriched stereoisomer" or "racemic isomer" of the various aforementioned stereoisomers. These stereoisomers can be prepared according to an asymmetric synthesis process, or separated, purified and enriched by a chiral separation process (including but not limited to thin layer chromatography, rotating chromatography, column chromatography, gas chromatography, high pressure liquid chromatography, etc.), as well as obtained by chiral separation by means of bonding (chemical binding etc.) or salifying (physical binding etc.) with other chiral compound (s). The term "pure stereoisomer" herein refers to that the mass content of a stereoisomer of the compound is no less than 95% relative to other stereoisomers of the compound. The term "enriched stereoisomer" herein refers to that the mass content of a stereoisomer of the compound is no less than 50% relative to other stereoisomers of the compound. The term "racemic isomer" herein refers to that the mass content of a stereoisomer of the compound is equal to that of another stereoisomer of the compound.

The term "isotopic compound" used herein refers to that there is one or more atomic isotopes with natural or non-natural abundance contained in the compound of formula I, or the pharmaceutically acceptable salt, solvate, polymorph, co-crystal, stereoisomer, metabolite or prodrug thereof. Atomic isotopes with non-natural abundance include, but are not limited to, deuterium ($^2H$ or D), tritium ($^3H$ or T), iodine-125 ($^{125}I$), phosphorus-32 ($^{32}P$), carbon-13 ($^{13}C$) or carbon-14 ($^{14}C$). The aforementioned isotopic compound can also be used as a therapeutic or diagnostic agent (i.e., internal developing agent) or research tool. All the isotopic variants of the compound of the invention, whether or not radioactive, are included in the scope of the invention.

The term "isotope enriched" used herein refers to that there is one or more atomic isotopes with non-natural abundance contained in the compound of formula I, or the pharmaceutically acceptable salt, solvate, polymorph, co-crystal, stereoisomer, isotopic compound, metabolite or prodrug thereof. The term "isotope enriched" also refers to that the compound of formula I, or the pharmaceutically acceptable salt, solvate, polymorph, co-crystal, stereoisomer, isotopic compound, metabolite or prodrug compound thereof, contains at least one isotopic atom with non-natural abundance.

As used herein, the term "patient" or "subject" refers to any animal to be treated or have been treated with the compound or the composition according to an embodiment of the invention, mammalian is preferable, and human is the most preferable. The term "mammalian" used herein includes any mammals. Examples of mammal include but are not limited to cattle, horse, sheep, pig, cat, dog, mice, rat, rabbit, guinea pig, monkey, human, etc., human is the most preferable. The terms "subject" and "patient" are used interchangeably herein.

In an embodiment, the terms "treat" and "treating" refers to an improvement, prevention or reversal of a disease or disorder or at least one of identifiable symptoms thereof, such as treating cancer by reducing or stabilizing the symptoms of cancer or a disease. In another embodiment, "treat" or "treating" refers to an improvement, prevention or reversal of at least one measurable body parameter of a disease or disorder which is being treated, the disease or disorder may not be identified in mammal. However, in another embodiment, the term "treat" or "treating" refers to slow the progress of a disease or disorder, in physical, such as stabilizing identifiable symptoms, or in physiological, such as stabilizing physical parameters, or in both. In another embodiment, the term "treat" or "treating" refers to delaying the onset of a disease or disorder.

In some embodiments, the compound is administered for a prevention purpose. As used herein, "prevent" or "preventing" refers to a reduction in a risk of given disease or symptom. In a preferred mode of embodiment, the designated compound is administered to a subject for a prevention purpose, such as the subject with family history or tendency of cancer or autoimmune disease.

As used herein, "therapeutically effective amount" refers to an amount of the compound or the composition that can cause a biological or medical response (which is sought by researchers, veterinarians, physicians, or other clinicians) for a tissue system, an animal or a person, where may include relieving symptoms of the disease or symptom which is being treated. In a preferred embodiment, the therapeutically effective amount is an amount which is enough to effectively treat, improvably treat or prevent cancer, symptom or disorder associated with undesirable angiogenesis or TNF-α.

The term "prophylactically effective amount" refers to an amount of an active compound or agent (sought by researchers, veterinarians, physicians or other clinicians), that can inhibit the onset of a disease in a subject. A prophylactically effective amount of a compound refers to an amount of a therapeutic agent used alone or in combination with other active compound, which can provide a therapeutic benefit for treating or preventing the disease, disorder or condition.

Unless otherwise specified, the singular form of the term used herein, "a" or "an", also includes a plural meaning.

Unless otherwise specified, the term "or" or "and" used herein refers to "and/or".

Unless otherwise specified, the "〜" or "━" in the specific group herein refers to a connection position.

The term "optional" or "optionally" means the event or circumstance described subsequent thereto may or may not happen. This term encompasses the cases that the event or circumstance may or may not happen. For example, "optional substitution" or "optionally substituted" encompasses the cases that being unsubstituted or substituted.

Deuterium (D or $^2H$) is a stable non-radioactive isotope of hydrogen, its atomic weight is 2.0144. Hydrogen exists in the form of an isotopic mixture of H (hydrogen or protium), D ($^2H$ or deuterium) and T ($^3H$ or tritium) in natural, where the deuterium abundance is 0.0156%. According to the common technical knowledge in the field, of all the compounds whose structures contain natural hydrogen atoms, the hydrogen atom actually represents a mixture of H, D and T. Therefore, if a compound contains a deuterium whose abundance greater than its natural abundance 0.0156% at any position, these compounds should be considered to be non-natural or deuterium enriched, and thus these compounds are novel relative to its non-enriched analogues.

In the invention, "deuterium enriched" compound refers to a compound of formula I, or the pharmaceutically acceptable salt, solvate, polymorph, co-crystal, stereoisomer, isotopic compound, metabolite or prodrug thereof, where the deuterium abundance is greater than its natural abundance at any relevant position. Therefore, in the "deuterium enriched" compound, the deuterium abundance at any of the relevant positions is likely between more than 0.0156% and 100%. The deuterium enriched position is represented by D, whereas the non-deuterium enriched position is represented by H. According to the common technical knowledge in the field, the symbol H may be elided at the non-deuterium enriched position. An example of a process for preparing a deuterium enriched compound is replacing the hydrogen with the deuterium, or employing deuterium-enriched starting material to synthesize the compound.

In the invention, the percentage of the deuterium in the enriched deuterium or the deuterium abundance refers to molar percentage.

In the invention, non-deuterium enriched refers to the hydrogen in natural, which is in the form of a mixture of isotopes H (hydrogen or protium), D ($^2$H or deuterium) and T ($^3$H or tritium).

Each preferred conditions aforementioned can be combined in any way without departing from the common knowledge in the art and thereby forming various preferred embodiments of the invention.

The reagents and starting materials used herein are all commercially available.

The positive effects achieved by the invention are that the compound of formula I can regulate the generation and/or activity of cytokines (e.g. TNF-α) so as to effectively treat cancer and inflammatory diseases.

DETAILED DESCRIPTION OF THE EMBODIMENTS

The invention will be further illustrated by the following examples, but it should not be constructed that the invention is limited to the scope of the examples. The experimental methods that are not specified in details in the following examples are those according to conventional methods and conditions, or according to the product manuals.

Example 1 Synthesis of Compound K101

Synthesis Scheme

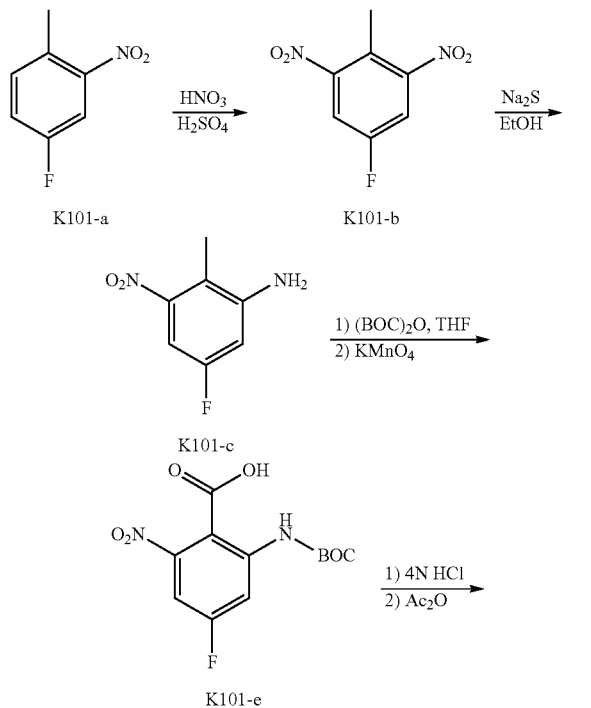

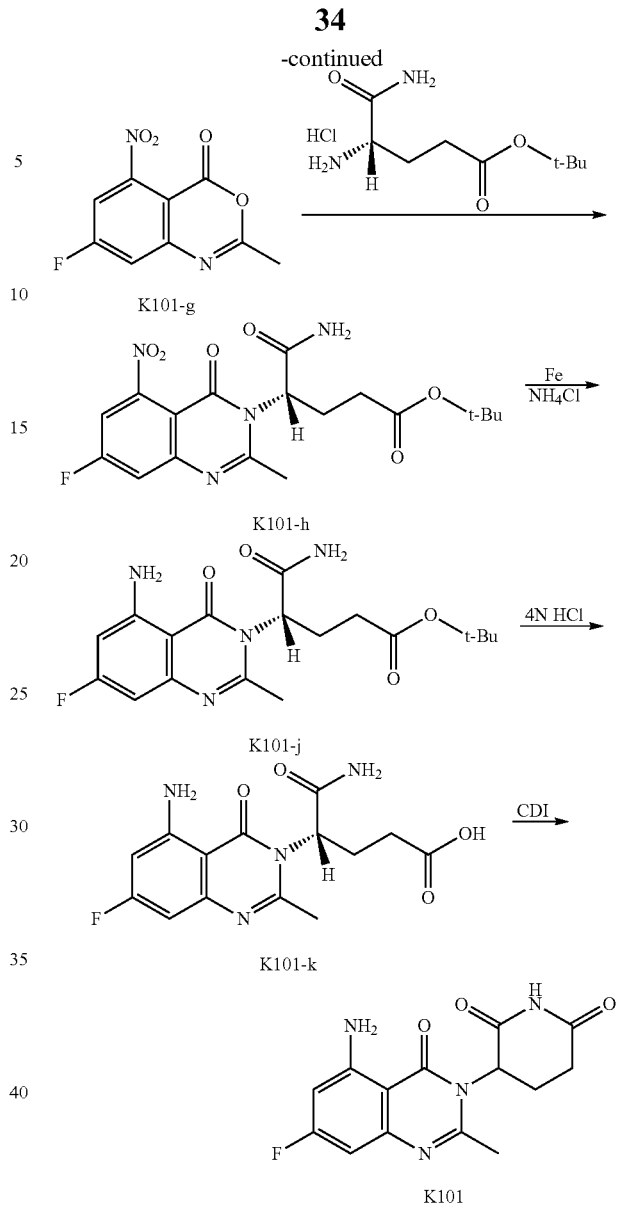

Step 1: Synthesis of Compound K101-b

To a solvent of K101-a (60 g, 38.7 mmol) in con. H$_2$SO$_4$ (150 mL), a mixture of con. HNO$_3$ (36 mL) and con. H$_2$SO$_4$ (200 mL) was added dropwise over 2 hours at 0° C. while the temperature of the reaction mixture was controlled at 0° C.-15° C. The reaction mixture was stirred for another 1 hour and quenched by pouring into crushed ice. Then the water layer was extracted with DCM (100 mL×2). The combined organic solution was dried over anhydrous Na$_2$SO$_4$, filtered and concentrated to afford a crude product, which was purified by chromatography column on silica gel to afford the product K101-b (16 g, 21%).

$^1$H NMR (CDCl3, 300 MHz): δ 7.78 (d, J=6.9 Hz, 2H), 2.55 (s, 3H).

Step 2: Synthesis of Compound K101-c

To a solution of K101-b (9.0 g, 45.0 mmol) in EtOH (100 mL), a solution of Na$_2$S (16.2 g, 67.5 mmol) in H$_2$O (50 mL) was added dropwise over 30 min at 25° C. The mixture was stirred for 4 hours, then concentrated to afford a crude product. The crude product was diluted with H$_2$O (200 mL) and extracted with EtOAc (100 mL×2), the combined organic layer was dried over anhydrous Na$_2$SO$_4$, filtered and concentrated, the residue was purified by chromatography column (PE/EtOAc=10/1) to afford the product K101-c (5.0 g, 65%).

$^1$H NMR (DMSO-d$_6$, 300 MHz): δ 6.84 (dd, J=6.3, 1.8 Hz, 1H), 6.68 (dd, J=8.4, 1.8 Hz, 1H), 5.90 (br s, 2H), 2.03 (s, 3H).

Step 3: Synthesis of Compound K101-e

To a solution of K101-c (1.60 g, 9.40 mmol) in THF (150 mL) was added (Boc)$_2$O (2.25, 10.0 mmol) and DMAP (1.15 g, 9.40 mmol). The mixture was stirred for 18 hours at 25° C. and concentrated to remove THF. The residue was diluted with EtOAc (200 mL), then washed with 1N/HCl (100 mL×2) and dried over anhydrous Na$_2$SO$_4$, filtered and concentrated to afford a crude product (1.7 g). The crude product was added to a mixture of pyridine (30 mL) and H$_2$O (15 mL). The mixture was heated to 80° C., then KMnO$_4$ (3.2 g, 19.8 mmol) was added in 4 batches over 2 hours (one batch every 30 minutes). The resulting mixture was stirred overnight. The reaction solution was filtered and the cake was washed with hot water. The filtrate was extracted with DCM (150 mL×3). The combined organic phase was dried over Na$_2$SO$_4$, filtered and concentrated to afford a crude product. The crude product was purified by chromatography column on silica gel (EtOAc/PE=1/5) to afford the product K101-e (1.0 g, 30% for 2 steps).

$^1$H NMR (CDCl$_3$, 300 MHz): δ 10.53 (br s, 1H), 8.01 (dd, J=11.4, 2.4 Hz, 1H), 7.46 (dd, J=7.8, 2.4 Hz, 1H), 1.45 (s, 9H).

Step 4: Synthesis of Compound K101-g

To a solution of 4N/HCl in 1,4-dioxane (80 mL) was added K101-e (1.0 g, 3.3 mmol). The mixture was stirred for 2 hours at 25° C. and concentrated to afford a crude product (800 mg). A mixture of the crude product and Ac$_2$O (10 mL) was heated to reflux and stirred for 4 hours. The reaction solution was concentrated and the residue was stirred with (EtOAc/Et$_2$O=1/2, 30 mL) for 30 min. The solid impurities were remove by filtration. The filtrate was concentrated to afford the product K101-g (670 mg, 91% for 2 steps)

$^1$H NMR (DMSO-d$_6$, 300 MHz): δ 8.14 (dd, J=8.1, 2.4 Hz, 1H), 7.74 (dd, J=9.0, 2.4 Hz, 1H), 2.42 (s, 3H).

Step 5: Synthesis of Compound K101-h

To a mixture of K101-g (500 mg, 2.23 mmol) in MeCN (25 mL) was added (S)-tert-butyl 4,5-diamino-5-oxopentanoate hydrochloride (640 mg, 2.68 mmol), imidazole (334 mg, 4.91 mmol) and triphenyl phosphite (832 mg, 2.68 mmol). The reaction solution was stirred at reflux for 16 hours. This mixture was concentrated and diluted with H$_2$O (150 mL) and extracted with EtOAc (100 mL×2). The combined organic layer was dried over anhydrous Na$_2$SO$_4$, filtered and concentrated. The residue was purified with chromatography column on silica gel (EtOAc/PE=1/3) to afford the product K101-h (600 mg, 66%).

$^1$H NMR (DMSO-d$_6$, 300 MHz): δ 7.98 (dd, J=8.7, 2.4 Hz, 1H), 7.68 (dd, J=9.9, 2.4 Hz, 1H), 7.42-7.49 (m, 1H), 7.13-7.21 (m, 1H), 4.68-4.92 (m, 1H), 2.54 (s, 3H), 2.05-2.43 (m, 4H), 1.28 (s, 9H).

Step 6: Synthesis of Compound K101-j

To a solution of K101-h (600 mg, 1.47 mmol) in EtOH (60 mL) was added saturated aq. NH$_4$Cl solution (20 mL). The mixture was heated to 80° C. and Fe powder (600 mg, 10.7 mmol) was added. The reaction mixture was heated with stirring for another 3 hours, filtered and concentrated to remove the majority of EtOH. The remaining mixture was extracted with EtOAc (150 mL×2). The combined organic layer was dried and concentrated to afford the product K101-j (540 mg, 97%)

$^1$H NMR (DMSO-d$_6$, 300 MHz): δ 6.97-7.50 (m, 4H), 6.30-6.33 (m, 2H), 4.56-4.73 (m, 1H), 2.44 (s, 3H), 2.06-2.32 (m, 4H), 1.32 (s, 9H).

Step 7: Synthesis of Compound K101-k

To a solution of 4N/HCl in 1,4-dioxane (20 mL) was added K101-j (540 mg, 1.43 mmol). This mixture was stirred at 25° C. for 2 hour, then concentrated to afford the product K101-k (492 mg).

$^1$H NMR (DMSO-d$_6$, 300 MHz): δ 7.12-7.56 (m, 4H), 6.64 (d, J=6.0 Hz, 1H), 6.51 (d, J=6.0 Hz, 1H), 4.80 (br s, 1H), 2.76 (s, 3H), 1.98-2.38 (m, 4H).

Step 8: Synthesis of Compound K101

To a solution of K101-k (400 mg, 1.24 mmol) in MeCN was added CDI (400 mg, 2.48 mmol). The reaction solution was heated to 95° C. and stirred overnight, then concentrated to afford a crude product. The crude product was purified by HPLC to afford the product K101 (210 mg, 56%).

$^1$H NMR (DMSO-d$_6$, 300 MHz): δ 10.99 (s, 1H), 7.32 (br s, 2H), 6.34 (d, J=10.8 Hz, 2H), 5.13-5.19 (m, 1H), 2.82-2.88 (m, 1H), 2.58-2.78 (m, 2H), 2.53 (s, 3H), 2.11-2.18 (m, 1H). LCMS: 305.1 ([M+1]$^+$).

Example 2 Synthesis of Compound K105

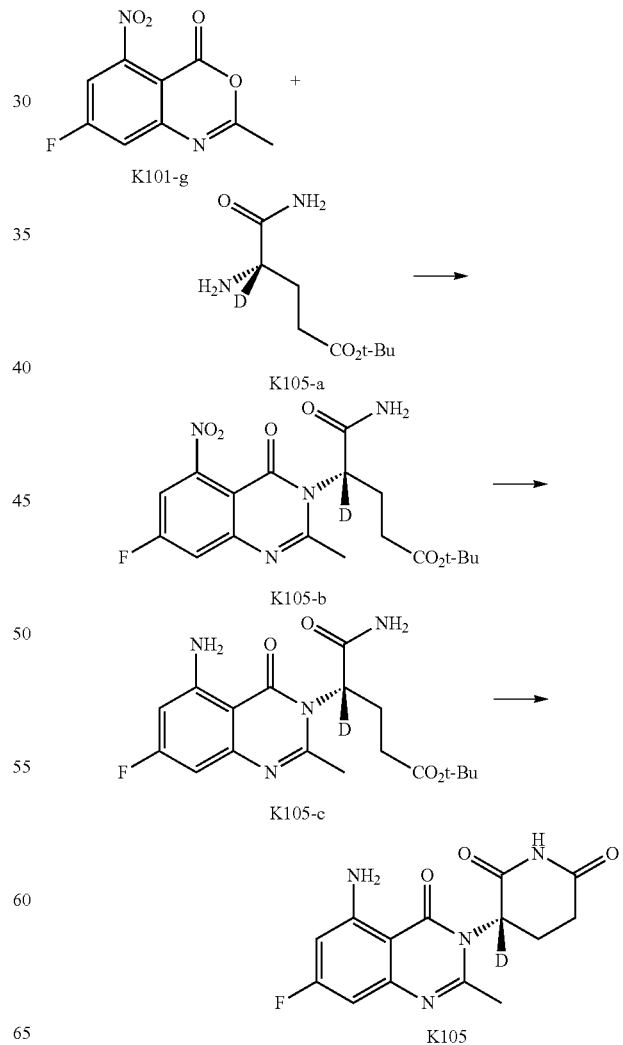

Step 1: Synthesis of Compound K105-b

To a mixture of K101-g (800 mg, 3.57 mmol) in CH₃CN (30 mL), K105-a (726 mg, 3.57 mmol), imidazole (533 mg, 7.85 mmol) and triphenyl phosphite (1.33 g, 4.28 mmol) were added. The reaction solution was stirred at reflux for 16 hour. This mixture was concentrated and diluted with EtOAc (500 mL), washed successively with water, saturated aq. NaHCO₃ solution and brine. The organic layer was dried over Na₂SO₄, filtered and concentrated. The residue was purified with chromatography column on silica gel (EtOAc/PE=1/1) to afford the product K105-b (480 mg, yield: 33%).

$^1$H NMR (DMSO-d$_6$, 300 MHz): δ 8.00 (dd, J=8.1, 2.4 Hz, 1H), 7.70 (dd, J=9.6, 2.1 Hz, 1H), 7.21-7.38 (m, 2H), 2.57 (s, 3H), 2.24-2.51 (m, 2H), 2.08-2.18 (m, 2H), 1.31 (s, 9H).

Step 2: Synthesis of Compound K105-c

To a solution of K105-b (480 mg, 1.17 mmol) in EtOH (60 mL) was added saturated aq. NH₄Cl solution (20 mL). The mixture was heated to 80° C. and Fe powder (6570 mg, 11.72 mmol) was added to the reaction solution. The mixture was stirred for 3 hour at 80° C., then cooled to room temperature, filtered and concentrated under reduced pressure to remove the majority of EtOH. The remaining water layer was extracted with EtOAc (100 mL×3). The combined organic layer was dried, filtered and concentrated. The residue was purified with chromatography column on silica gel (EtOAc/PE=1/1) to afford the product K105-c (437 mg, yield: 98%)

$^1$H NMR (DMSO-d$_6$, 300 MHz): δ 7.07-7.49 (m, 4H), 6.30-6.35 (m, 2H), 2.45 (s, 3H), 2.07-2.34 (m, 4H), 1.33 (s, 9H).

Step 3: Synthesis of Compound K105

To a solution of 6N/HCl in 1,4-dioxane (30 mL) was added K105-c (437 mg, 1.15 mmol). This mixture was stirred at 25° C. for 2 hours, and then concentrated. The residue was dissolved in DMF (3 mL) and DCM (30 mL). The mixture was cooled to −40° C., and SOCl₂ (685 mg, 5.76 mmol) in DCM (2 mL) was added dropwise. Then the mixture was reacted at −40~−30° C. for 1.5 hours. Pyridine (912 mg, 11.52 mmol) in DCM (2 mL) was added and the mixture was stirred at −40~−30° C. for 1 hour. Et₃N (237 mg, 2.7 mmol) in DCM (1 mL) was added and the mixture was stirred at −40~−30° C. for 1 hour. H₂O (10 mL) was then added to quench the reaction. The mixture was concentrated under reduced pressure to afford a crude product. The crude product was purified by Prep-HPLC to afford K105 (68 mg).

$^1$H NMR (DMSO-d$_6$, 400 MHz): δ 10.94 (br s, 1H), 7.35 (br s, 2H), 6.36 (s, 1H), 6.33 (s, 1H), 5.14-5.19 (m, 0.21H), 2.87-2.77 (m, 1H), 2.63-2.54 (m, 2H), 2.51 (s, 3H), 2.11-2.16 (m, 1H). MS: 306.1 ([M+1]$^+$).

Example 3 Synthesis of Compound K102

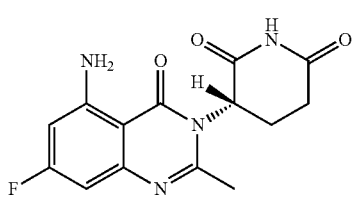

K102

Compound K102 was synthesized by a similar method as K105 described in Example 2 except the corresponding substrate was used instead of compound K105-a in step 1.

$^1$H NMR (DMSO-d$_6$, 400 MHz): δ 11.01 (s, 1H), 7.32 (br s, 2H), 6.32-6.36 (m, 2H), 5.16 (dd, J=11.6, 5.6 Hz, 1H), 2.78-2.83 (m, 1H), 2.57-2.66 (m, 2H), 2.54 (s, 3H), 2.08-2.17 (m, 1H). MS: 305.1 ([M+1]$^+$).

Example 4 Synthesis of Compound K106

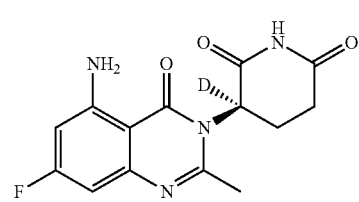

K106

Compound K106 was synthesized by a similar method as compound K105 described in Example 2 except the corresponding substrate

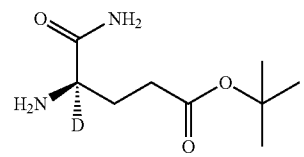

was used instead of K105-a in step 1.

$^1$H NMR (400 MHz, DMSO-d6) δ 11.03 (s, 1H), 7.34 (br s, 2H), 6.36 (s, 1H), 6.33 (s, 1H), 5.14-5.18 (m, 0.11H), 2.76-2.87 (m, 1H), 2.59-2.63 (m, 2H), 2.54 (s, 3H), 2.13-2.17 (m, 1H). LCMS: 306.0 ([M+1]+).

Example 5 Synthesis of Compound K103

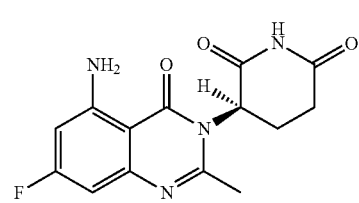

K103

Compound K103 was synthesized by a similar method as compound K105 described in Example 2 except the corresponding substrate

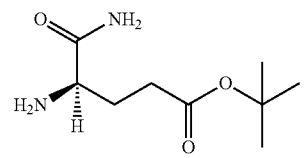

was used instead of K105-a in step 1.

$^1$H NMR (400 MHz, DMSO-d6) δ 11.00 (s, 1H), 7.32 (br s, 2H), 6.36 (s, 1H), 6.33 (s, 1H), 5.14-5.18 (m, 1H), 2.78-2.87 (m, 1H), 2.59-2.67 (m, 2H), 2.54 (s, 3H), 2.08-2.17 (m, 1H). LCMS: 305.1 ([M+1]+).

Example 6 Synthesis of Compound K104

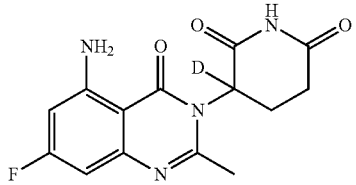
K104

Compound K104 was synthesized by a similar method as compound K105 described in Example 2 except the corresponding substrate

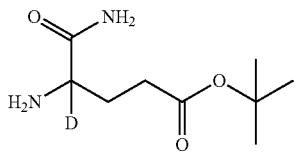

was used instead of K105-a in step 1.

$^1$H NMR (400 MHz, DMSO-d6) δ 11.01 (s, 1H), 7.33 (brs, 1H), 6.33-6.36 (m, 2H), 2.79-2.83 (m, 1H), 2.57-2.62 (m, 2H), 2.53 (s, 3H), 2.12-2.16 (m, 1H). LCMS: 306.1 ([M+1]+).

Example 7 Synthesis of Compound K501

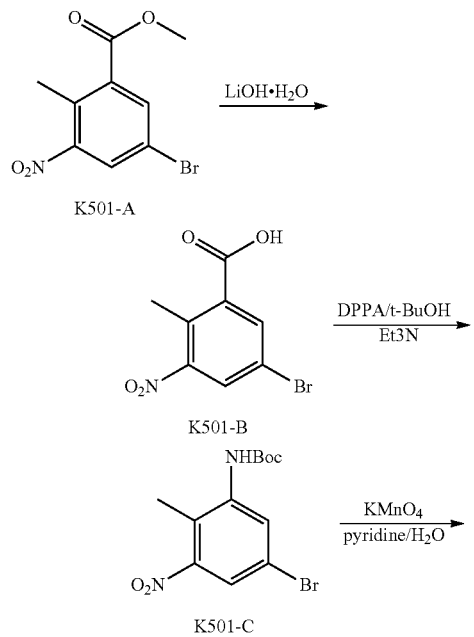

Step 1: Synthesis of Compound K501-B

To the solution of compound K501-A (14.0 g, 51.1 mmol) in THF (90 mL) was added LiOH (6.4 g, 153 mmol) and H$_2$O (30 mL). The reaction mixture was stirred at 25° C. overnight and then concentrated. The remaining liquid was diluted with Et$_2$O (60 mL) and water (100 mL). The organic layer was separated. The water layer was adjusted with 2N HCl to pH=2, extracted with EtOAc (150 mL). The organic layers were washed with sat. brine (200 mL), dried, filtered and concentrated to afford K501-B (12.9 g) as yellow solid.

$^1$H NMR (400 MHz, DMSO-d$_6$): δ 8.30 (d, J=2.0 Hz, 1H), 8.14 (d, J=2.0 Hz, 1H), 2.45 (s, 3H)

Step 2: Synthesis of Compound K501-C

To the solution of K501-B (12.9 g, 49.61 mmol) in t-BuOH (200 mL) was added phosphorazidic acid diphenyl ester (20.5 g, 74.42 mmol) and Et$_3$N (7.5 g, 74.4 mmol). The mixture was stirred at 80° C. overnight. The reaction solution was concentrated and the remaining liquid was diluted with EtOAc (300 mL) and water (200 mL), the organic layer was washed with sat. brine (200 mL), dried, filtered and concentrated. The solid residue was purified by column chromatography on silica gel PE:EA (10:1) to afford K501-C (15.3 g) as yellow solid.

$^1$H NMR (400 MHz, CDCl$_3$) δ 8.34 (s, 1H), 7.64 (d, J=2.0 Hz, 1H), 6.46 (s, 1H), 2.29 (s, 3H), 1.53 (s, 9H).

Step 3: Synthesis of Compound K501-D

To a mixture of pyridine (300 mL) and $H_2O$ (150 mL) was added K501-C (15.3 g, 46.2 mmol). This mixture was heated to 80° C., $KMnO_4$ (29.2 g, 184.8 mmol) was added in 6 batches over 3 hours (one batch every 30 minutes). The resulting mixture was stirred overnight and then the reaction solution was filtered. The filter cake was washed with EtOAc (800 mL) and hot water (200 mL). The combined filtrate was concentrated and adjusted with 1N HCl to pH=2, extracted with EtOAc (800 mL). The combined organic layer was dried over $Na_2SO_4$ then filtered and concentrated to afford the solid residue. The residue was purified by column chromatography on silica gel (PE:EA 30:1-5:1) to afford K501-D (9.8 g) as yellow solid.

$^1$H NMR (400 MHz, DMSO-$d_6$) δ 9.55 (s, 1H), 8.29 (d, J=2.0 Hz, 1H), 7.91 (d, J=2.0 Hz, 1H), 1.47 (s, 9H).

Step 4: Synthesis of Compound K501-E

To a solution of K501-D in DCM (100 mL) was added $CF_3COOH$ at 0° C. The mixture was reacted overnight at 25° C., then concentrated. HCl in 1,4-dioxane (30 ml) was added. The mixture was stirred for 20 min at 25° C., then concentrated to afford K501-E (6.7 g).

$^1$H NMR (400 MHz, DMSO-$d_6$) δ 7.19-7.24 (m, 1H), 7.11-7.13 (m, 1H).

Step 5: Synthesis of Compound K501-F

A solution of K501-E (2.8 g) in $Ac_2O$ (20 mL) and HOAc (60 mL) was heated to reflux and stirred for 3 hours. The reaction solution was concentrated and the residue was stirred and slurried in EtOAc:PE (2:1, 15 mL) for 1 hour, then filtered to afford K501-F (2.3 g) as yellow solid.

$^1$H NMR (400 MHz, DMSO-$d_6$) δ 8.36 (d, J=1.6 Hz, 1H), 8.08 (d, J=2.0 Hz, 1H), 2.42 (s, 3H).

Step 6: Synthesis of Compound K501-G

To a mixture of K501-F (500 mg, 1.75 mmol), 3-aminopiperidine-2,6-dione hydrochloride (433 mg, 2.63 mmol) in $CH_3CN$ (20 mL) was added imidazole (262 mg, 3.86 mmol), $(PhO)_3P$ (816 mg, 2.63 mmol). The mixture was stirred for 16 hours at 85° C. After the reaction was completed, the solvent was removed in vacuum. To the residue was added 9 mL of EtOAc and 9 mL of $H_2O$, the mixture was stirred and slurried for 1 hour and filtered to afford K501-G (382 mg, crude) as gray solid.

Step 7: Synthesis of Compound K501

A mixture of K501-G in HOAc (15 mL) was heated to 80° C., and then Fe powder (965 mg, 17.3 mmol) was added. The mixture was reacted for 2 hours, then filtered to remove Fe powder. HOAc was removed in vacuum to afford a crude product. The crude product was purified by column chromatography on silica gel ($CH_3CN$:DCM 1:1) to give a product which was further purified by prep-HPLC to afford K501 (180 mg).

$^1$H NMR (400 MHz, DMSO-$d_6$): δ 11.00 (s, 1H), 7.24 (s, 2H), 6.74 (dd, J=13.2, 1.6 Hz, 2H), 5.15-5.19 (m, 1H), 2.78-2.87 (m, 1H), 2.59-2.65 (m, 2H), 2.58 (s, 3H), 2.14-2.18 (m, 1H). LCMS: 367.0 ([M+2]$^+$).

Example 8 Synthesis of Compound K401

Compound K401 was synthesized by a similar method as compound K501 described in Example 7 except the corresponding starting material 5-chloro-2-methyl-3-nitrobenzoic acid was used instead of compound K501-B.

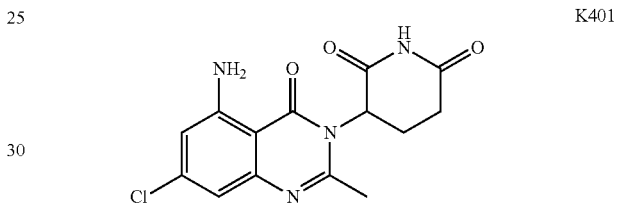

$^1$H NMR (400 MHz, DMSO-$d_6$): δ 11.00 (s, 1H), 7.24 (br s, 2H), 6.76 (d, J=1.6 Hz, 1H), 6.73 (d, J=1.6 Hz, 1H), 5.15-5.19 (m, 1H), 2.82-2.83 (m, 1H), 2.58-2.62 (m, 2H), 2.54 (s, 3H), 2.07-2.16 (m, 1H). LCMS: 321.0 ([M+1]$^+$).

Example 9 Synthesis of Compound K633 and K635

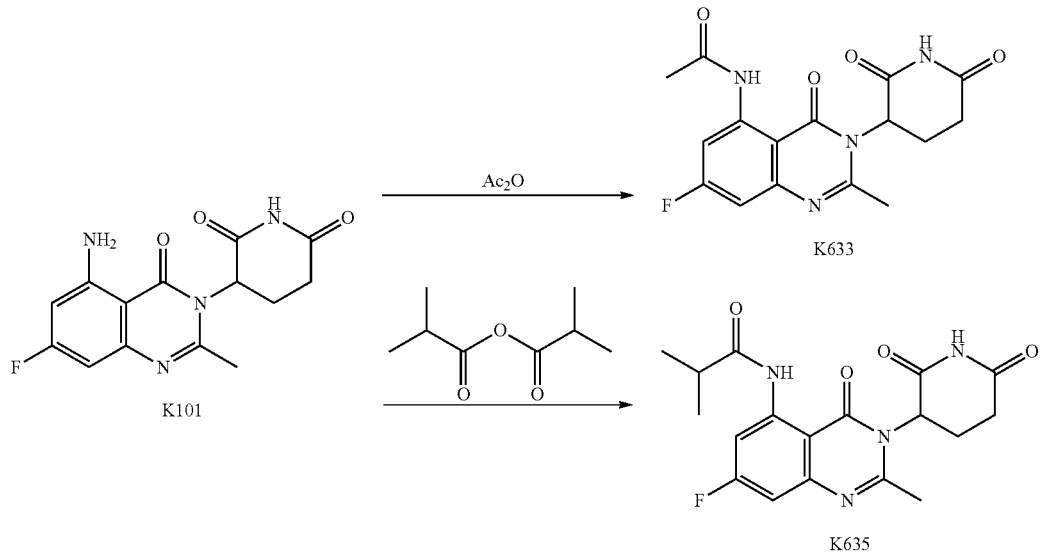

Synthesis of Compound K633

To a solution of K101 (300 mg, 0.99 mmol) in 10 mL of DMF was added Ac$_2$O (1 mL). The mixture was heated to 50° C. in oil bath and reacted for 5 hours, cooled to 25° C. and concentrated to dryness under reduced pressure. The residue was recrystallized from CH$_3$CN and then purified by prep-HPLC to afford K633 (250 mg).

$^1$H NMR (DMSO-d$_6$, 400 MHz): δ 11.82 (s, 1H), 11.09 (s, 1H), 8.36 (dd, J=12.8, 2.4 Hz, 1H), 7.08 (dd, J=9.6, 2.4 Hz, 1H), 5.32-5.36 (m, 1H), 2.81-2.91 (m, 1H), 2.61-2.73 (m, 5H), 2.19-2.23 (m, 4H). LCMS: 347.1 [(M+1)]+.

Synthesis of Compound K635

Compound K635 was synthesized by a similar method as compound K633 except the corresponding substrate isobutyric anhydride was used instead of Ac$_2$O.

$^1$H NMR (DMSO-d$_6$, 400 MHz): δ 11.96 (s, 1H), 11.11 (s, 1H), 8.39 (dd, J=12.4, 2.4 Hz, 1H), 7.08 (dd, J=9.6, 2.8 Hz, 1H), 5.34 (dd, J=11.6, 5.6 Hz, 1H), 2.81-2.90 (m, 1H), 2.51-2.73 (m, 6H), 2.17-2.23 (m 1H), 1.16 (d, J=7.2 Hz, 6H). LCMS: 375.0 [(M+1)]+.

Example 10 Synthesis of Compound K627

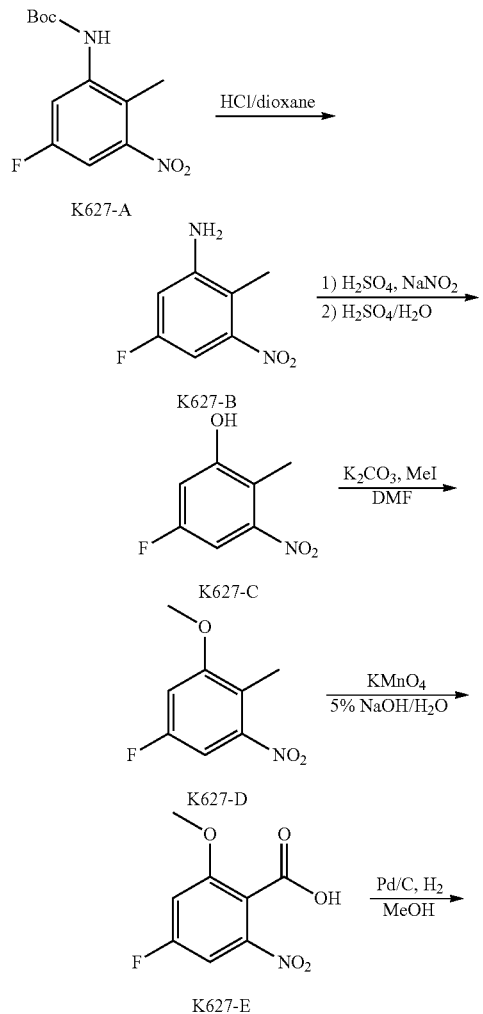

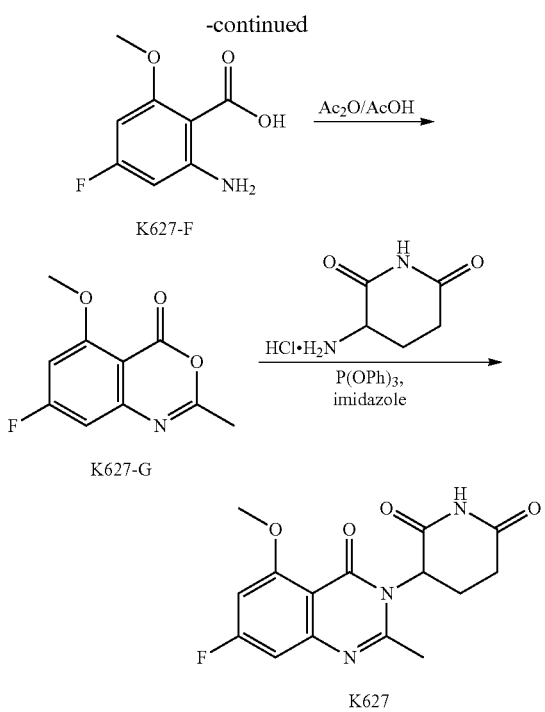

Step 1: Synthesis of Compound K627-B

K627-A (10.0 g, 37.0 mmol) was dissolved in HCl/dioxane (5 M, 100 mL) and stirred at 15° C. for 2 hours. The solvent was removed by rotary evaporation. The residue was slurried with PE (100 mL) at 15° C. for 1 hour to afford the product K627-B (7.1 g) as solid.

$^1$H NMR (400 MHz, DMSO-d$_6$) δ 8.26 (br s, 2H), 6.92 (dd, J=8.8, 2.8 Hz, 1H), 6.79 (dd, J=11.4, 2.8 Hz, 1H), 2.06 (s, 3H).

Step 2: Synthesis of Compound K627-C

To a mixed solvent of conc. H$_2$SO$_4$ (75 mL) and water (37 mL) was added K627-B (6.5 g) at 0° C. NaNO$_2$ (2.86 g, 42 mmol) was added slowly and the reaction solution was stirred at 0° C. for another 2 hours. The mixture was heated to 115° C. and H$_2$SO$_4$ (50%, 110 mL) was added dropwise. Then the mixture was stirred at 115° C. for another 2 hours. After cooled to room temperature, the mixture was extracted with EtOAc (300 mL×2). The organic layer was washed with sat. brine (300 mL), dried over anhydrous Na$_2$SO$_4$, filtered and concentrated to afford a crude product K627-C (5.4 g).

$^1$H NMR (400 MHz, DMSO) δ 10.91 (s, 1H), 7.26 (dd, J=8.4, 2.4 Hz, 1H), 6.93 (dd, J=10.0, 2.4 Hz, 1H), 2.18 (s, 3H).

Step 3: Synthesis of Compound K627-D

K627-C (5.4 g, 31.6 mmol) and K$_2$CO$_3$ (21.8 g, 158 mmol) were dissolved in DMF (100 mL). To the mixture was added CH$_3$I (13.5 g, 94.7 mmol) at 0° C. The mixture was stirred at 20° C. overnight, then concentrated under reduced pressure to remove the solvent. The residue was dissolved with EtOAc (500 mL), washed with water (300 mL×2) and sat. brine (300 mL), dried and concentrated to afford K627-D (5.23 g) as brown solid.

$^1$H NMR (400 MHz, DMSO-d$_6$) δ 7.39-7.41 (m, 1H), 7.28-7.31 (m, 1H), 3.90 (s, 3H), 2.19 (s, 3H).

Step 4: Synthesis of Compound K627-E

To a mixed solution of KMnO$_4$ (13.6 g, 86 mmol) and H$_2$O (550 mL) was added K627-D (5.2 g, 28.1 mmol) and 5% NaOH aqueous solution (55 mL). This mixture was heated at refluxed for 3 hours. The reaction solution was filtered and the filter cake was washed with hot water (100 mL×2), the filtrate was adjusted with 2 N HCl to pH=2, extracted with EtOAc (500 mL×3). The combined organic layer was dried over anhydrous Na$_2$SO$_4$, filtered and concentrated to afford K627-E (2.5 g) as yellow solid.

$^1$H NMR (400 MHz, DMSO-d$_6$) δ 13.70 (br s, 1H), 7.64 (dd, J=8.8, 2.4 Hz, 1H), 7.56 (dd, J=10.8, 2.4 Hz, 1H), 3.91 (s, 3H).

Step 5: Synthesis of Compound K627-F

K627-E (2.5 g, 11.6 mmol) was dissolved in MeOH (30 mL), and 10% Pd/C (0.5 g, 50% water) was added. The mixture was stirred overnight at 25° C. under H$_2$ atmosphere (50 psi). The mixture was filtered. The filtrate was concentrated by rotary evaporation to obtain K627-F (1.9 g) as white solid.

$^1$H NMR (400 MHz, DMSO-d$_6$) δ 6.14 (dd, J=11.6, 2.4 Hz, 1H), 6.07 (dd, J=11.6, 2.4 Hz, 1H), 3.75 (s, 3H).

Step 6: Synthesis of Compound K627-G

Compound K627-F (1.9 g, 10.3 mmol) was dissolved in Ac$_2$O (20 mL) and AcOH (60 mL). The mixture was heated to 100° C. and reacted for 6 hours. The mixture was concentrated by rotary evaporation to give a solid. The solid was dispersed in EtOAc (5 mL) and PE (5 mL), stirred for 0.5 hour at 20° C., filtered to obtain K627-G (1.96 g) as yellow solid.

$^1$H NMR (400 MHz, DMSO-d$_6$) δ 7.09 (dd, J=12.0, 2.4 Hz, 1H), 6.90 (dd, J=9.6, 2.4 Hz, 1H), 3.93 (s, 3H), 2.34 (s, 3H).

Step 7: Synthesis of Compound K627

K627-G (250 mg, 1.2 mmol), 3-aminopiperidine-2,6-dione hydrochloride (257 mg, 1.56 mmol), imidazole (245 mg, 3.6 mmol) and triphenyl phosphate (1.12 g, 3.6 mmol) in CH$_3$CN (20 mL) was heated at reflux overnight under N$_2$. The mixture was cooled to 25° C. and concentrated to dryness by rotary evaporation. The residue was purified by silica gel chromatography (EtOAc) to afford a crude product. The crude product was further purified by prep-HPLC to afford K627 (168 mg).

$^1$H NMR (300 MHz, DMSO-d$_6$) δ 10.98 (s, 1H), 6.88-6.94 (m, 2H), 5.12-5.18 (m, 1H), 3.85 (s, 3H), 2.77-2.87 (m, 1H), 2.57-2.64 (m, 5H), 2.08-2.15 (m, 1H). LCMS: 320.1 [(M+1)]+.

Example 11 Synthesis of Compound K631

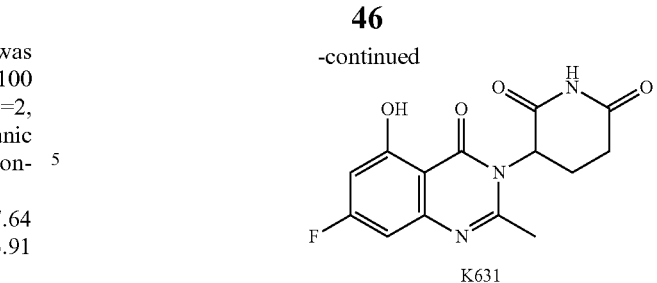

Step 1: Synthesis of Compound K631-G

Compound K627-G (1.0 g, 4.78 mmol), tert-butyl 4,5-diamino-5-oxopentanoate (1.26 g, 6.21 mmol), imidazole (0.98 g, 14.34 mmol) and triphenyl phosphate (4.45 g, 14.34 mmol) was dissolved in CH$_3$CN (100 mL), then the mixture was refluxed overnight under N$_2$. The mixture was cooled to 25° C. and concentrated to dryness by rotary evaporation. The residue was purified by silica gel chromatography (PE:EtOAc 1:1) to afford K631-G (1.18 g) as off-white solid.

$^1$H NMR (400 MHz, DMSO-d$_6$) δ 6.99-7.36 (m, 2H), 6.83-6.91 (m, 2H), 4.67 (br s, 1H), 3.86 (s, 3H), 2.43-2.45 (m, 3H), 2.07-2.31 (m, 4H), 1.32 (s, 9H).

Step 2: Synthesis of Compound K631

K631-G (600 mg, 1.53 mmol) was dissolved in DCM (10 mL). BBr$_3$ (1.15 g, 4.6 mmol) was added at 0° C. The mixture was stirred at 50° C. overnight and then poured into ice (10 g). The solvent was removed by rotary evaporation. Water (20 mL) was added to the residue. The mixture was stirred at 25° C. for 3 hours, filtered and the solid was purified by prep-HPLC to afford K631 (80 mg) as off-white solid.

$^1$H NMR (300 MHz, DMSO-d$_6$) δ 11.48 (br s, 1H), 11.17 (br s, 1H), 6.90 (dd, J=10.2, 2.4 Hz, 1H), 6.78 (dd, J=11.1, 2.4 Hz, 1H), 5.33-5.39 (m, 1H), 2.85-2.86 (m, 1H), 2.58-2.80 (m, 5H), 2.19-2.26 (m, 1H). LCMS: 306.1 [(M+1)]+

Example 12 Synthesis of Compound K700

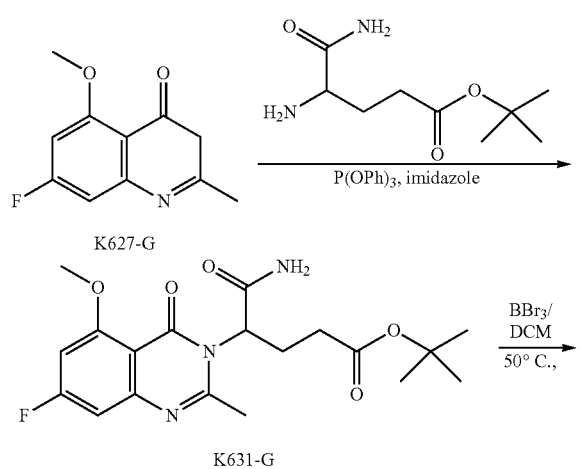

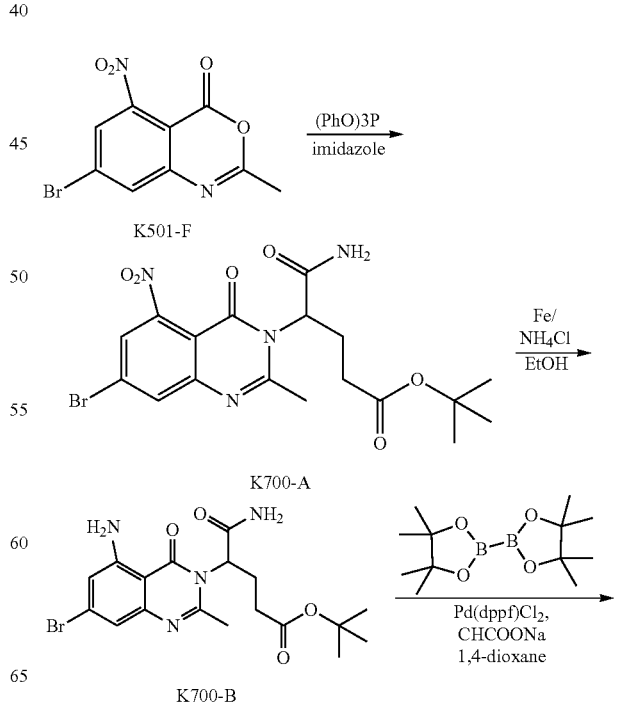

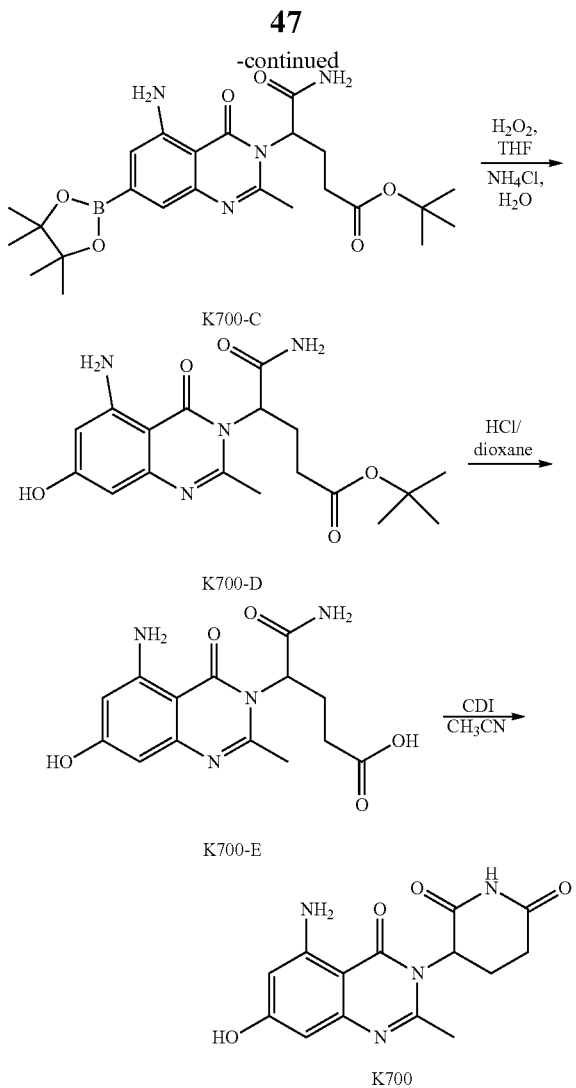

purified by column chromatography on silica gel (PE:EtOAc 1:1~1:5) to afford the K700-B (994 mg) as yellow solid.

$^1$H NMR (300 MHz, DMSO-$d_6$) δ 7.37-7.42 (m, 1H), 7.22-7.33 (m, 2H), 7.02-7.06 (m, 1H), 6.69-6.73 (m, 2H), 4.70 (br s, 1H), 2.44 (s, 3H), 2.02-2.37 (m, 4H), 1.32 (s, 9H).

Step 3: Synthesis of Compound K700-C

To a solution of K700-B (894 mg, 2.04 mmol) in dioxane (50 mL), was added bis(pinacolato)diboron (1.03 g, 4.07 mmol), $CH_3CO_2K$ (399 mg, 4.07 mmol) and Pd(dppf)$Cl_2$ (156 mg, 0.20 mmol). The mixture was heated to 100° C. under Ar and reacted for 3 hours. The reaction solution was filtered and concentrated to afford a crude product, which was purified by column chromatography on silica gel DCM: MeOH (20:1) to afford the K700-C (1.26 g).

Step 4: Synthesis of Compound K700-D

To a solution of K700-C (1.45 g, 2.98 mmol) in THF (30 mL), was added $NH_4Cl$ (159 mg, 2.98 mmol) in $H_2O$ (15 mL), and $H_2O_2$ (22.5 mL) was added dropwise at 25° C. The mixture was stirred overnight. The mixture was washed by aq. $Na_2SO_3$ solution and extracted with EtOAc (150 mL×3). The combined organic layer was dried, concentrated and purified by prep-HPLC to afford K700-D (437 mg) as yellow solid.

$^1$H NMR (300 MHz, DMSO-$d_6$) δ 9.86 (s, 1H), 7.31-7.36 (m, 1H), 6.97-7.03 (m, 3H), 5.99 (s, 2H), 4.56 (br s, 1H), 2.39 (s, 3H), 2.05-2.27 (m, 4H), 1.34 (s, 9H).

Step 5: Synthesis of Compound K700-E

To a solution of 8N HCl in 1,4-dioxane (20 mL) was added K700-D (300 mg, 0.80 mmol). The mixture was stirred for 2 hours at 40° C., and then concentrated to afford crude product K700-E (307 mg).

Step 6: Synthesis of Compound K700

To a mixture of K700-E (307 mg, 0.96 mmol) in $CH_3CN$ (20 mL) was added CDI (466 mg, 2.88 mmol) at 25° C. The mixture was heated to 85° C. and reacted overnight. To the reaction solution was added $H_2O$ (20 mL). The mixture was heated to 60° C. and reacted for 3 hours, concentrated and purified by prep-HPLC to afford a crude product, which was then stirred and slurried in $CH_3CN$ (5 mL) for 1 hour to afford K700 (119 mg) as yellow solid.

$^1$H NMR (400 MHz, DMSO-$d_6$) δ 10.91 (s, 1H), 9.92 (s, 1H), 6.93 (s, 2H), 5.99-6.01 (m, 2H), 5.04-5.08 (m, 1H), 2.76-2.81 (m, 1H), 2.55-2.61 (m, 2H), 2.48 (s, 3H), 2.009-2.13 (m, 1H). LCMS: 303.0 ([M+1]$^+$).

Example 13 Synthesis of Compound K613

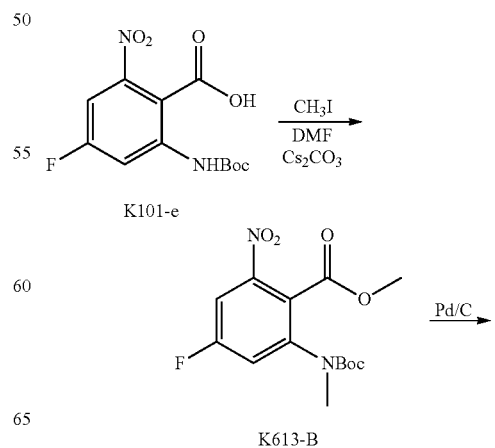

Step 1: Synthesis of Compound K700-A

To a solution of K501-F (500 g, 1.754 mmol), tert-butyl 4,5-diamino-5-oxopentanoate (433 mg, 2.631 mmol) in $CH_3CN$ (40 mL) was added imidazole (525 mg, 7.717 mmol), (PhO)$_3$P (1.3 g, 4.209 mmol). The reaction mixture was heated to 85° C. and reacted for 16 hours. When the reaction was completed, the solvent was removed via vacuum. To the residue was added EtOAc (100 mL) and $H_2O$ (50 mL). The organic phase was separated and washed with sat. NaHCO$_3$ aqueous solution (50 mL), dried and concentrated to afford a crude product. The crude product was purified by column chromatography on silica gel (PE: EtOAc 3:1-1:1) to afford K700-A (1.29 g) as yellow solid.

$^1$H NMR (400 MHz, DMSO-$d_6$) δ 8.19 (d, J=2.0 Hz, 1H), 8.07 (d, J=2.0 Hz, 1H), 7.47 (br s, 1H), 7.19 (br s, 1H), 4.83 (br s, 1H), 2.56 (s, 3H), 2.27-2.47 (m, 2H), 2.20-2.23 (m, 1H), 2.07-2.09 (m, 1H), 1.23 (s, 9H).

Step 2: Synthesis of Compound K700-B

To a solution of K700-A (1.29 g, 2.76 mmol) in EtOH (180 mL), was added sat. aq. $NH_4Cl$ solution (60 ml). The mixture was heated to 80° C. and Fe powder (1.54 g, 27.6 mmol) was added. The mixture was reacted for 3 hours. Then the reaction solution was filtered to remove Fe powder. EtOH was removed via vacuum. The residue was extracted with EtOAc (150 mL), partitioned, dried, concentrated, and

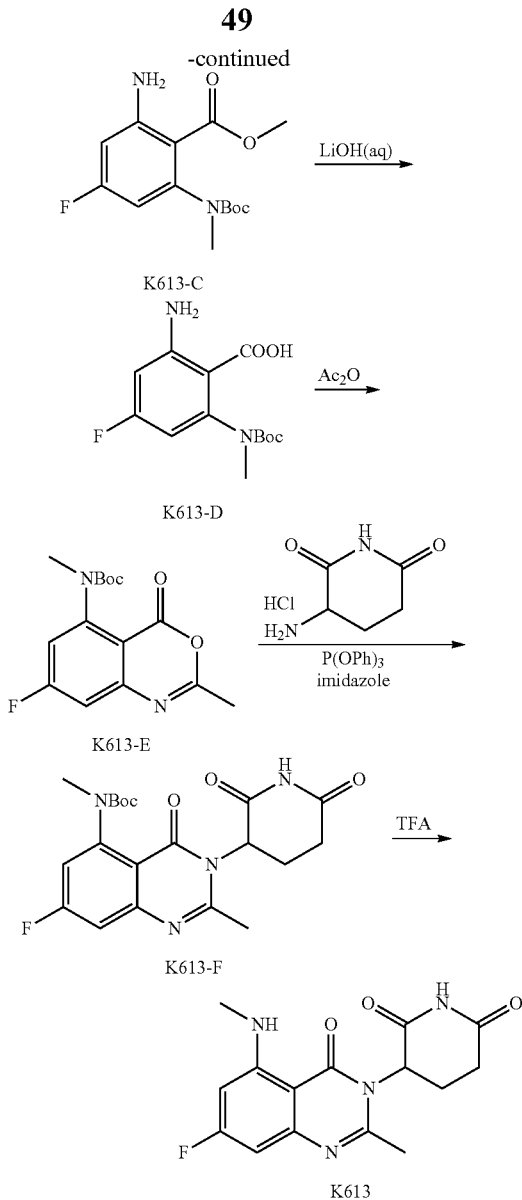

Step 1: Synthesis of Compound K613-B

K101-e (3.4 g, 11.32 mmol) was dissolved in 30 mL of DMF at 25° C., and Cs$_2$CO$_3$ (9.23 g, 28.31 mmol) was added. The mixture was stirred for 30 min. CH$_3$I (2.1 mL, 34.0 mmol) was added. The mixture was stirred at 25° C. overnight, diluted with 200 mL of EtOAc, washed successively with water and sat. brine, dried over anhydrous Na$_2$SO$_4$, concentrated to dryness to afford K613-B (3.5 g).

$^1$H NMR (DMSO-d$_6$, 300 MHz): δ 8.09 (d, J=9.3 Hz, 1H), 7.92 (d, J=9.6 Hz, 1H), 3.80 (s, 3H), 3.10 (s, 3H), 1.28 (s, 9H).

Step 2: Synthesis of K613-C

To a solution of K613-B (3.5 g, 10.66 mmol) in 100 mL of MeOH was added 10% Pd/C (700 mg, 50% water). The mixture was stirred overnight under H$_2$ atmosphere at 50 psi. Pd/C was removed by filtration, the filtrate was concentrated to dryness to afford product K613-C (3.0 g).

$^1$H NMR (DMSO-d$_6$, 300 MHz): δ 6.43-6.48 (m, 1H), 6.38 (s, 2H), 6.29-6.33 (m, 1H), 3.72 (s, 3H), 3.03 (s, 3H), 1.24 (s, 9H).

Step 3: Synthesis of Compound K613-D

To a solution of K613-C (3.0 g, 10 mmol) in 60 mL of MeOH and 20 mL of H$_2$O was added LiOH.H$_2$O (2.11 g, 50.2 mmol). The mixture was heated to 70° C. and reacted for 5 hours, then cooled to 25° C., and 50 mL of H$_2$O was added. The mixture was concentrated to remove MeOH, and then cooled with ice-water, adjusted with 2N HCl to pH=2. A solid precipitation was formed. Filtration was conducted. The solid was washed with cold water and petroleum ether, then dried to afford product K613-D (2.8 g).

$^1$H NMR (DMSO-d$_6$, 300 MHz): δ 6.40-6.45 (m, 1H), 6.27 (dd, J=9.6, 2.4 Hz, 1H), 3.03 (s, 3H), 1.26 (s, 9H).

Step 4: Synthesis of Compound K613-E

K613-D (2.8 g, 9.85 mmol) was dissolved in 50 mL of Ac$_2$O. The mixture was heated to 50° C. and reacted for 5 hours, then cooled to 25° C. and concentrated to dryness to afford crude product K613-E (3.0 g), which was used directly in the next step.

Step 5: Synthesis of Compound K613-F

K613-E (3.0 g, 9.85 mmol) was dissolved in 50 mL of CH$_3$CN. To the mixture was immediately added 3-aminopiperidine-2,6-dione hydrochloride (2.43 g, 14.78 mmol), triphenyl phosphite (6.72 g, 21.67 mmol) and imidazole (2.01 g, 29.55 mmol). The mixture was refluxed overnight, then cooled to 25° C. and concentrated to dryness. 50 mL of icy water and 30 mL of petroleum ether/EtOAc (1:1) was added. The mixture was stirred for 30 min, filtered, washed successively with icy water and petroleum ether:EtOAc (1:1), and dried to afford product K613-F (2.8 g).

Step 6: Synthesis of Compound K613

K613-F (2.8 g) was dissolved in 50 mL DCM, cooled with ice-water, and 50 mL of TFA was added dropwise. Then the reaction solution was stirred at 25° C. for 2 hours and concentrated to dryness. Then 20 mL icy water was added and the mixture was basified with sat. NaHCO$_3$. A solid precipitation was formed. Filtration was conducted. The solid was washed with icy water and petroleum ether, dried and purified by prep-HPLC to afford K613 (719 mg) as white solid.

$^1$H NMR (400 MHz, DMSO-d$_6$) δ 11.01 (s, 1H), 8.47 (s, 1H), 6.38 (dd, J=10.0, 2.4 Hz, 1H), 6.26 (dd, J=12.8, 2.4 Hz, 1H), 5.19 (dd, J=11.2, 6.0 Hz, 1H), 2.80-2.84 (m, 4H), 2.56-2.65 (m, 5H), 2.13-2.19 (m, 1H). LCMS: ([M+1]+) =319.2

Example 14 Synthesis of Compound K617

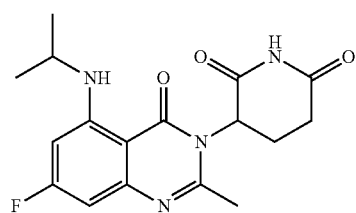

K617

Compound K617 was synthesized by a similar method as compound K613 described in Example 13 except (CH$_3$)$_2$CHI was used instead of CH$_3$I in step 1.

$^1$H NMR (400 MHz, DMSO-d$_6$) δ 11.02 (s, 1H), 8.52 (d, J=6.4 Hz, 1H), 6.35-6.38 (m, 2H), 5.17-5.21 (m, 1H), 3.67-3.72 (m, 1H), 2.79-2.83 (m, 1H), 2.55-2.63 (m, 5H), 2.11-2.17 (m, 1H), 1.18-1.20 (m, 6H). LCMS: [(M+1)]+= 347.0

Example 15 Synthesis of Compound K704

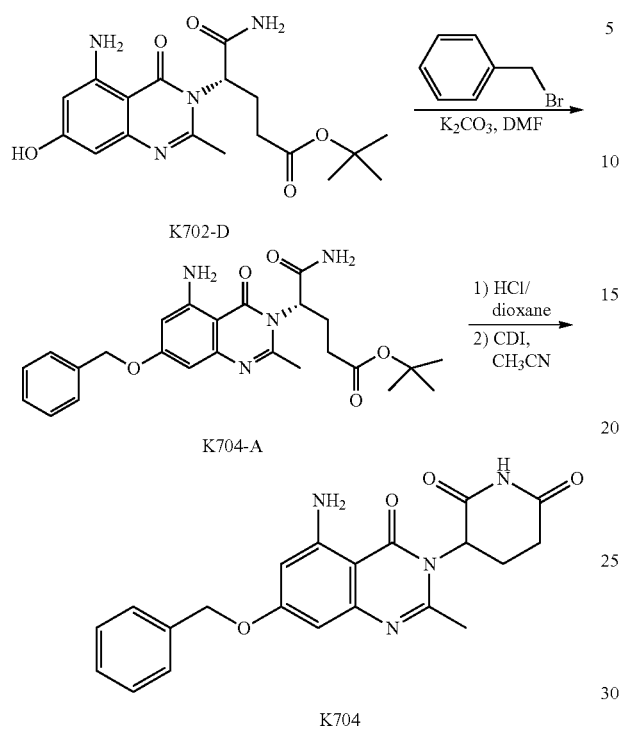

The starting material K702-D was synthesized by a similar method as compound K700-D described in Example 12 except (S)-tert-butyl 4,5-diamino-5-oxopentanoate hydrochloride was used instead of tert-butyl 4,5-diamino-5-oxopentanoate in step 1.

$^1$H NMR (300 MHz, DMSO-d$_6$) δ 9.85 (s, 1H), 7.35 (br s, 1H), 6.98-6.99 (m, 3H), 5.98 (s, 2H), 4.54 (br s, 1H), 2.10-2.38 (m, 7H), 1.33 (s, 9H).

Step 1: Synthesis of Compound K704-A

To a mixture of K702-D (800 mg, 2.12 mmol) in DMF (15 mL), was added K$_2$CO$_3$ (352 mg, 2.55 mmol) and benzyl bromide (436 mg, 2.55 mmol) at 25° C. The mixture was reacted at 25° C. for 16 hours. The reaction solution was quenched with ice-water (100 mL) and then extracted with EtOAc (100 mL), dried, concentrated and purified by column chromatography on C18 to afford K704-A (567 mg).

$^1$H NMR (400 MHz, DMSO-d$_6$) δ 7.32-7.44 (m, 6H), 7.06 (br s, 3H), 6.19-6.22 (m, 2H), 5.14 (s, 2H), 4.60 (br s, 1H), 2.05-2.41 (m, 7H), 1.33 (s, 9H).

Step 2: Synthesis of Compound K704

To a solution of 4.5N/HCl in 1,4-dioxane (20 mL) was added K704-A (567 mg, 1.2 mmol). The mixture was stirred for 4 hours at 25° C. After concentration, 15 mL of CH$_3$CN was added and then concentrated (repeated for three times) to afford a crude product (570 mg). The crude product was dissolved in MeCN (15 mL). CDI (675 mg, 4.17 mmol) was added. The mixture was heated to 85° C. and reacted overnight. Icy water (100 mL) was added and the mixture was extracted with EtOAc (70 mL×2), dried and concentrated to afford a crude product which was purified by column chromatography on C18 to afford the crude product. The crude product was purified by Prep-HPLC to afford K704 (71 mg).

$^1$H NMR (400 MHz, DMSO-d$_6$) δ 10.96 (s, 1H), 7.35-7.43 (m, 5H), 7.02 (br s, 2H), 6.21-6.24 (m, 2H), 5.04-5.18 (m, 3H), 2.77-2.81 (m, 1H), 2.51-2.62 (m, 5H), 2.08-2.11 (m, 1H). LC-MS: 393.0 ([M+1]$^+$).

Example 16 Synthesis of Compound K706

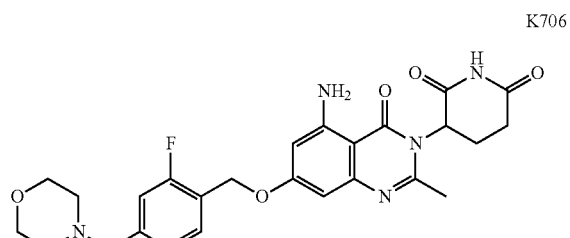

Compound K706 was synthesized by a similar method as compound K704 described in Example 15 except the corresponding substrate was used instead of benzyl bromide in step 1.

$^1$H NMR (400 MHz, DMSO-d$_6$) δ 10.96 (s, 1H), 7.48 (t, J=8.0 Hz, 1H), 7.16-7.20 (m, 2H), 7.02 (s, 2H), 6.27 (d, J=2.4 Hz, 1H), 6.19 (d, J=2.4 Hz, 1H), 5.09-5.13 (m, 3H), 3.56-3.59 (m, 4H), 3.49 (s, 2H), 2.76-2.87 (m, 1H), 2.55-2.61 (m, 2H), 2.51 (s, 3H), 2.36 (s, 4H), 2.08-2.17 (m, 1H). LCMS: 510.0 ([M+1]$^+$).

Example 17 Synthesis of Compound K720

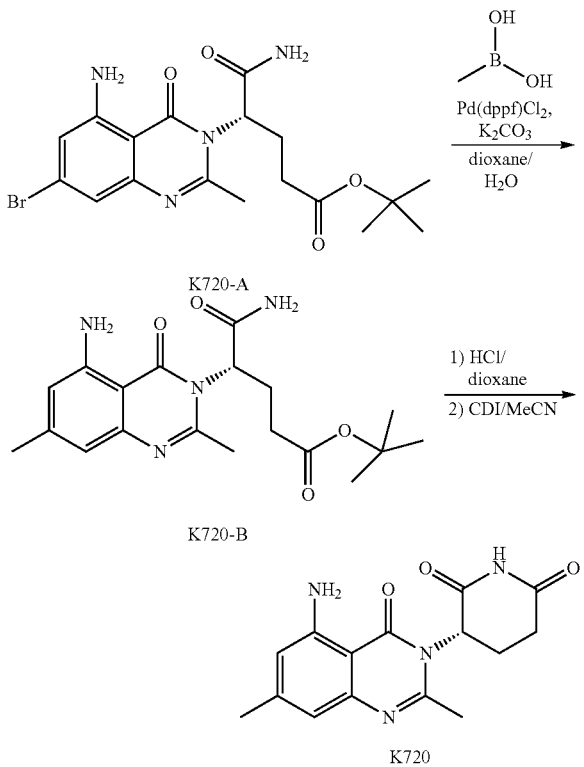

Compound K720-A was synthesized by a similar method as compound K700-B described in Example 12 except (S)-tert-butyl 4,5-diamino-5-oxopentanoate hydrochloride was used instead of tert-butyl 4,5-diamino-5-oxopentanoate.

Step 1: Synthesis of Compound K720-B

K720-A (1.5 g, 3.4 mmol), methylboronic acid (1.23 g, 3.4 mmol), Pd(dppf)Cl$_2$ (0.5 g, 0.68 mmol), K$_2$CO$_3$ (0.94 g, 6.8 mmol) was dissolved in the mixture solution of dioxane (20 mL) and water (5 mL). The mixture was heated at 100° C. under N$_2$ overnight. Water (100 mL) was added. The mixture was extracted with EtOAc (100 mL×2), dried, concentrated and purified by column chromatography on silica gel (PE:EtOAc 1:2) to afford compound K720-B (0.8 g).

$^1$H NMR (300 MHz, DMSO-d$_6$) δ 6.96-7.39 (m, 4H), 6.40 (s, 1H), 6.36 (s, 1H), 4.61 (br s, 1H), 2.09-2.50 (m, 10H), 1.33 (s, 9H).

Step 2: Synthesis of Compound K720

Compound K720-B (0.8 g, 2.13 mmol) was added to HCl/dioxane solution (4.5 N, 100 mL). The mixture was stirred at 20° C. for 3 hours and concentrated to remove the solvent. The residue was dissolved in CH$_3$CN (60 mL). CDI (0.69 g, 4.26 mmol) was added to the solution. The reaction solution was heated to 80° C. and stirred overnight. The mixture was concentrated and then purified by Prep-HPLC to afford the product K720 (85 mg) as off-white solid.

$^1$H NMR (400 MHz, DMSO-d$_6$) δ 10.97 (s, 1H), 6.94 (br s, 2H), 6.44 (s, 1H), 6.39 (s, 1H), 5.12 (dd, J=11.2, 6.0 Hz, 1H), 2.78-2.87 (m, 1H), 2.58-2.62 (m, 2H), 2.52 (s, 3H), 2.24 (s, 3H), 2.10-2.16 (m, 1H). LCMS: [(M+1)+]=301.0

Example 18 Synthesis of Compound K722

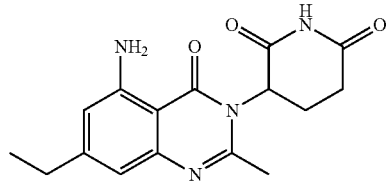
K722

Compound K722 was synthesized by a similar method as compound K720 described in Example 17 except ethylboronic acid was used instead of methylboronic acid in step 1.

$^1$H NMR (400 MHz, DMSO-d$_6$) δ 10.97 (s, 1H), 6.94 (s, 2H), 6.47 (s, 1H), 6.42 (s, 1H), 5.12 (dd, J=11.2, 6.0 Hz, 1H), 2.78-2.82 (m, 1H), 2.51-2.63 (m, 7H), 2.11-2.14 (m, 1H), 1.16 (t, J=7.6 Hz, 3H). LCMS: [(M+1)+]=315.0.

Example 19 Synthesis of Compound K724

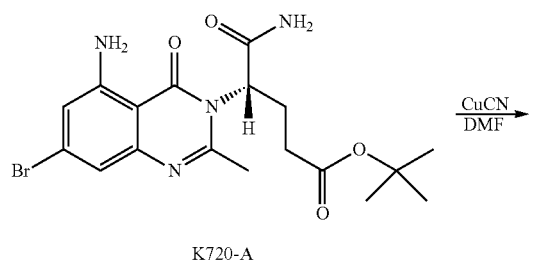
K720-A

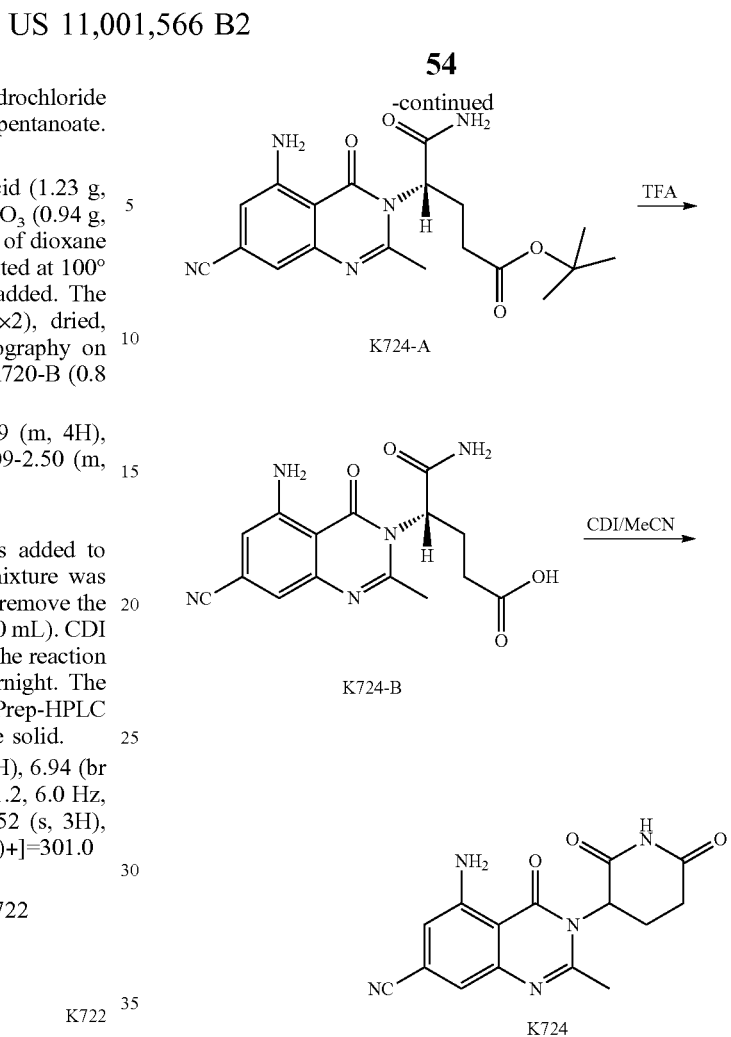

Step 1: Synthesis of Compound K724-A

To a solvent of K720-A (1.0 g, 2.28 mmol) and CuCN (1.02 g, 11.4 mmol) in DMF (30 mL) was reacted at 140° C. under N$_2$ overnight. H$_2$O (200 mL) was added. The mixture was extracted with EtOAc (100 mL×2), washed with sat. brine (100 mL×2), dried, concentrated and purified by column chromatography on silica gel (PE:EtOAc 1:3) to afford the product K724-A (0.24 g) as yellow solid.

$^1$H NMR (400 MHz, DMSO-d$_6$) δ 7.05-7.44 (m, 4H), 6.90 (d, J=1.6 Hz, 1H), 6.83 (d, J=1.6 Hz, 1H), 4.71 (br s, 1H), 2.16-2.48 (m, 7H), 1.32 (s, 9H).

Step 2: Synthesis of Compound K724-B

To a solution of compound K724-A (0.22 g, 0.57 mmol) in DCM (10 mL) was added TFA (10 mL). The mixture was stirred at 20° C. for 4 hours, then concentrated and purified by C$_{18}$ column (CH$_3$CN:H$_2$O 10:90) to afford the product K724-B (0.18 g) as yellow solid.

Step 3: Synthesis of Compound K724

To a solution of K724-B (180 mg, 0.547 mmol) in CH$_3$CN (40 mL) was added CDI (133 mg, 0.82 mmol). The reaction solution was heated to 80° C. and stirred overnight, then concentrated and purified by prep-HPLC to afford K724 (45 mg).

$^1$H NMR (400 MHz, DMSO-d$_6$) δ 11.05 (s, 1H), 7.42 (s, 2H), 6.93 (d, J=1.6 Hz, 1H), 6.85 (d, J=2.0 Hz, 1H), 5.22 (dd, J=11.2, 5.6 Hz, 1H), 2.79-2.88 (m, 1H), 2.57-2.65 (m, 5H), 2.14-2.20 (m, 1H). LCMS: ([M+1]+)=312.0

Example 20 Synthesis of Compounds K402-K406 and Compounds K502-K506

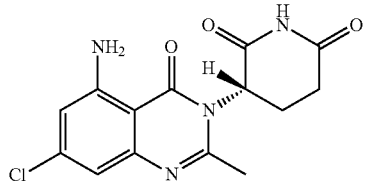
K402

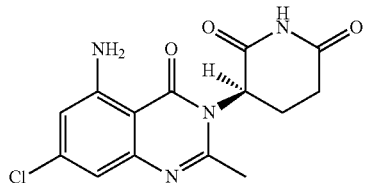
K403

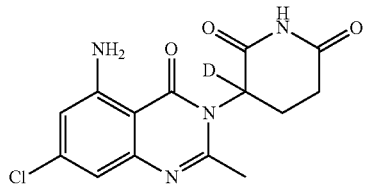
K404

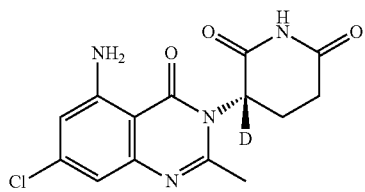
K405

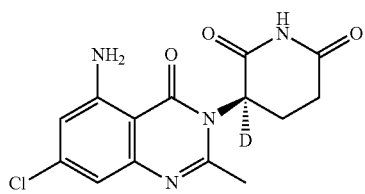
K406

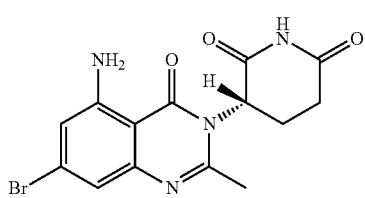
K502

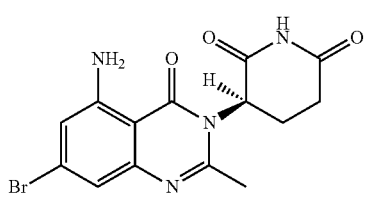
K503

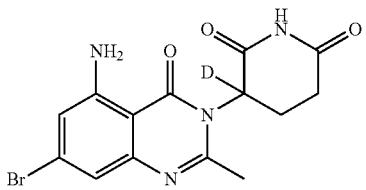
K504

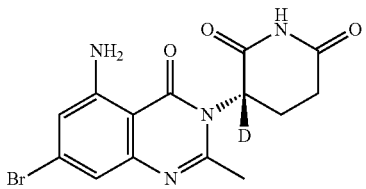
K505

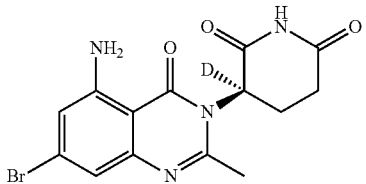
K506

These compounds were synthesized by a similar method as compound K105 described in Example 2 except the starting compounds

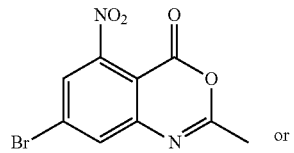
K501-F or

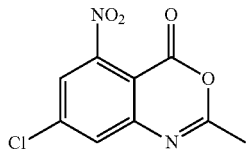
K401-F were used instead of compound K101-g in step 1, and corresponding substrates were used to replace K105-a. K401-F was synthesized by a similar method as compound K501-F described in

Efficacy Example 1: TNF-α Activity Inhibition Assay

Reagents for the Assay
  DPBS (10×): Invitrogen, Cat #14190
  RPMI 1640: RPMI Medium 1640 (1×), liquid, GIBCO, Cat #22400-105
  Heat Inactivated FBS: Invitrogen, Cat #10100147
  DMSO: Dimethyl sulphoxide, Sigma, Cat #D8418
  LPS: Sigma, Cat #L6529
  Pen/Strep (100×): Gibco, Cat #15140
  hPBMC: CTL, Cat #CTL-UP1
  CTL-Anti-Aggregate Wash 20×: CTL, Cat #CTL-AA-005

Human TNF ELISA Set: BD, Cat #555212
PBMC Recovery and Cell Plating Steps
1. Cell recovery
1) Agitation was performed continuously in a 37° C. water bath to rapidly thaw cells.
2) The cells were gently added to a 15 ml centrifuge tube, to which was then added 10 ml of fresh, prewarmed recovery medium gently and then centrifugation was performed at 1000 rpm for 10 min.
3) The supernatant medium was discarded and resuspension was performed with 10 ml of fresh, prewarmed RPMI 1640 complete medium.
2. 96-well plate plating
1) The total number of cells needed for the experiment was calculated and adjusted to the appropriate cell concentration per ml. 100 ul and $10^5$ cells per well.
2) The cell suspension was diluted with appropriate volume of cell culture medium.
3) The cell suspension was added to a disposable sterile sample well.
4) 100 ul of cell suspension was added to each well of a 96-well plate.
5) The plate was incubated in a 37° C., 5% $CO_2$ incubator for 2 hours.

Compound Preparation Step
1. LPS: The 1 mg/mL stock solution was diluted with water, aliquoted, and stored at −80° C. Prior to each test, the working solution of LPS was diluted from the stock solution with serum-free RPMI 1640 medium.
2. Test compound
20 mM stock solution was dissolved in DMSO and the compound was checked for solubility, aliquoted, and stored at −80° C.
8× compound gradient preparation:
A series of compound concentration gradient was diluted with DMSO: 10 mM, 2 mM, 0.4 mM, 80 uM, 16 uM, 3.2 uM, 0.64 uM, 0.128 uM were obtained and then the compounds were diluted 125-fold with serum-free RPMI 1640 medium to the final 8×. The final concentration of DMSO in cell culture was 0.1%.

Compound Processing Experimental Procedures and Collection of Supernatants
1. Cell Plating: Fresh cells were plated in 96-well cell culture plates according to the procedure above, 100 ul and $10^5$ cells per well, and then incubated in a 37° C., 5% $CO_2$ incubator for 2 hours.
2. Compound Preparation: Before test, compounds were added to the plates according to the above description. A dose of compound in 8× concentration was prepared with serum-free RPMI 1640 medium and all gradients of solution were added to the compound plate.
3. Compound addition: 16.7 ul of compound solution in working concentration was added to each well of the cell culture plate. The plate was incubated in a 37° C., 5% $CO_2$ incubator for 1 hour.
4. 16.7 ul of 8×LPS per well (final concentration of LPS is EC80, the amount of each PBMC needed to be determined) was added. The plate was incubated for 18 hours in 37° C., 5% $CO_2$ incubator.
5. 80 ul of supernatant per well was collected and then subjected to TNF-α ELISA assay. The collected supernatant can be stored at −80° C. The supernatant needed to be diluted in various ratios to ensure that the experimental dose would not exceed the linear range of the TNF-α standard curve, depending on the amount of TNF-α released in different donors. Typically, 20-100 ul of supernatant was diluted to 200 ul and then used for ELISA experiments.

TNF-α ELISA Step
The TNF-α ELISA test procedure were referred to the BD human TNF-α ELISA kit experimental procedure.
Experimental Design
Four compounds per plate. 5-fold dilution was performed, starting from 10 uM, by 8 gradients, and parallel wells were made. A total of 16 compounds were tested.
The TNF-α standard was added to each plate. (1st well, starting from 500 pg/ml, 2-fold dilution, 7 gradients)
ZPE (0% inhibition) used 15 pg/ml LPS+0.1% DMSO, while HPE (100% inhibition) used only 0.1% DMSO.
The inhibition rate statistics were calculated. The inhibition rate (%)=[1−(Max−Min)/(Test cpd−Min)]*100%. IC50 was used to evaluate the concentration of the test compound (nM) at 50% inhibition. The two experimental results are shown in Table 1 and Table 1-1.
In the present efficacy example and efficacy example 2, the structures corresponding to the codes for the compound of the invention are all as described above. The codes and structures of the reference compounds are summarized in Table N.

TABLE N

| Code | Structure |
| --- | --- |
| K001 | [structure image] |
| B001 | [structure image] |
| Reference 1 | [structure image] |
| Reference 2 | [structure image] |
| Reference 3 | [structure image] |

TABLE 1

| Compound | IC$_{50}$ value for TNF-α Inhibition (nM) |
|---|---|
| K101 | 27.77 |
| K001 | 32.54 |
| B001 | 192.5 |

TABLE 1-1

| Compound | IC$_{50}$ value for TNF-α Inhibition (nM) |
|---|---|
| K001 | 32.8 |
| B001 | 99.1 |
| K101 | 10.2 |
| K102 | 7.3 |
| K105 | 6.4 |
| K103 | 282.7 |
| K106 | 781.4 |
| K501 | 9.6 |
| K401 | 10.2 |
| K633 | 392.5 |
| Reference 1 | 2803 |
| K720 | 137.8 |
| K613 | 9.4 |
| K704 | 465.5 |
| K724 | 5.9 |
| K706 | 319.2 |
| K617 | 152.7 |

Efficacy Example 2: CTG Cell Proliferation Experimental Method

MM.1S cells (myeloma cells) (ATCC, catalog number CRL-2974), DOHH2 cells (mantle cell lymphoma cells) (DSMZ, catalog number ACC-47), NCI-H929 cells (myeloma cells) (ATCC, catalog number CRL-9068), or WSU-DLCL-2 cells (diffuse large B cell lymphoma cells) (DSMZ, catalog number ACC-575), Namalwa.CSN/70 cells (non-Hodgkin's lymphoma cells (DSMZ, catalog number ACC-70) was inoculated as (1.8-15)×10$^3$ per well in white wall, transparent bottom 96-well plate containing specific media (Corning, catalog number CLS3903), which was cultured in 37° C., 5% CO$_2$ incubator for 24 hours. Compounds were formulated in DMSO (Sigma, Cat. No. 276855) as 150 mM stock, which was diluted to the required concentration (DMSO final concentration is 0.2%) in culture medium and added to each well, 2 wells/concentration. The plate was incubated in 37° C., 5% CO$_2$ incubator for 72-120 hours. Afterwards, 100 µl of CellTiter-Glo® cell activity assay reagent (Promega, Cat. No. G7570) was added to each well, which was mixed on a plate shaker for 10 minutes to induce cell lysis. The 96-well plate was allowed to stand at room temperature for 10 minutes to stabilize the luminescence signal. A white base film was pasted on the bottom of the plate and the EnSpire was used to read the plate. Data processing was performed with XLfit software to obtain IC$_{50}$ values. The specific experimental data for various batches are shown in Table 2, Table 3, and Table 4.

TABLE 2

| Compound | IC$_{50}$ value for MM.1S Inhibition (µM) | IC$_{50}$ value for WSU-DLCL2 Inhibition (µM) | IC$_{50}$ value for DOHH2 Inhibition (µM) | IC$_{50}$ value for NCI-H929 Inhibition (µM) | IC$_{50}$ value for Namalwa.CSN/70 Inhibition (µM) |
|---|---|---|---|---|---|
| K101 | 0.0133 | 0.1793 | 0.1254 | 0.0304 | 0.0068 |
| B001 | 0.3618 | >300 | >300 | 1.0021 | >300 |
| K001 | 0.0498 | 0.4691 | 0.4589 | 0.0861 | 0.0658 |

TABLE 3

| Compound | IC$_{50}$ value for MM.1S Inhibition (µM) |
|---|---|
| K001 | 0.0375 |
| Reference 1 | 2.4035 |
| Reference 2 | >300 |
| Reference 3 | 1.170 |
| K627 | 5.929 |
| K633 | 0.3144 |
| K635 | 2.8118 |
| K700 | 0.5068 |
| K401 | 0.022 |
| K501 | 0.0267 |
| K631 | 0.9565 |

TABLE 4

| Compound | IC$_{50}$ value for MM.1S Inhibition (µM) |
|---|---|
| K001 | 0.275 |
| K102 | 0.104 |
| K105 | 0.033 |
| K104 | 0.192 |
| K106 | 0.504 |
| K103 | 0.465 |

The invention claimed is:
1. A compound of Formula I, or a pharmaceutically acceptable salt, solvate, stereoisomer, or isotopic compound thereof:

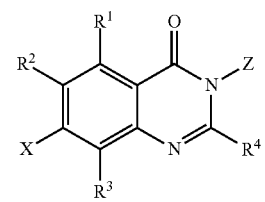

I wherein,
X is selected from the group consisting of halogen, hydroxyl, cyano, substituted or unsubstituted C$_1$-C$_6$ alkyl, and C$_1$-C$_6$ alkoxy substituted with 6-10 membered aryl; wherein the 6-10 membered aryl in the C$_1$-C$_6$ alkoxy substituted with 6-10 membered aryl is optionally substituted with one or more selected from the group consisting of D, halogen, hydroxyl, cyano, substituted or unsubstituted $C_1$-$C_6$ alkyl, and substituted or unsubstituted $C_1$-$C_6$ alkoxy, wherein when more than one substituents are present, they are identical or different;

Z is

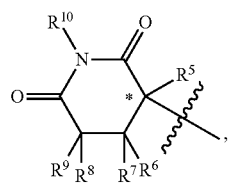

wherein the carbon marked with * is asymmetric center;

$R^1$ is selected from the group consisting of hydroxyl, substituted or unsubstituted $C_1$-$C_6$ alkoxy and —$NR^{1'}R^{2'}$; wherein $R^{1'}$ and $R^{2'}$ are each independently selected from the group consisting of H, D, substituted or unsubstituted $C_1$-$C_6$ alkyl and —$C(O)R^{3'}$; $R^{3'}$ is substituted or unsubstituted $C_1$-$C_6$ alkyl;

$R^2$, $R^3$, $R^5$, $R^6$, $R^7$, $R^8$, $R^9$, and $R^m$ are each independently H or D;

$R^4$ is $CH_3$, $CH_2D$, $CHD_2$ or $CD_3$;

wherein the substituted in the above substituted or unsubstituted $C_1$-$C_6$ alkoxy and the above substituted or unsubstituted $C_1$-$C_6$ alkyl independently represents substitution with one or more selected from the group consisting of D, halogen, amino, hydroxyl, cyano, $C_1$-$C_6$ alkoxy, and 4-10 membered heterocycloalkyl, wherein when more than one substituents are present, they are identical or different.

2. The compound of Formula I according to claim 1, or the pharmaceutically acceptable salt, solvate, stereoisomer, or isotopic compound thereof, wherein the halogen in X is fluorine, chlorine, bromine or iodine;

and/or when the 6-10 membered aryl is optionally substituted with halogen, the halogen is fluorine, chlorine, bromine or iodine;

and/or when the substituted in the substituted or unsubstituted $C_1$-$C_6$ alkoxy and the substituted or unsubstituted $C_1$-$C_6$ alkyl independently represents substitution with halogen, the halogen is fluorine, chlorine, bromine or iodine;

and/or the $C_1$-$C_6$ alkyl in the substituted or unsubstituted $C_1$-$C_6$ alkyl is $C_1$-$C_4$ alkyl;

and/or the $C_1$-$C_6$ alkoxy in the substituted or unsubstituted $C_1$-$C_6$ alkoxy is $C_1$-$C_4$ alkoxy;

and/or the 4-10 membered heterocycloalkyl is selected from the group consisting of 5-6 membered heterocycloalkyl, wherein the heteroatom is one or more selected from the group consisting of N, O and S, and wherein the number of heteroatom is 1 or 2;

and/or the $C_1$-$C_6$ alkoxy substituted with 6-10 membered aryl is selected from the group consisting of $C_1$-$C_4$ alkoxy substituted with phenyl; wherein the phenyl is optionally substituted with one or more of the following groups: D, halogen, hydroxyl, cyano, or $C_1$-$C_4$ alkyl substituted with pyrrolidinyl, piperidinyl, piperazinyl or morpholinyl, wherein when more than one substituents are present, they are identical or different.

3. The compound of Formula I according to claim 1, or the pharmaceutically acceptable salt, solvate, stereoisomer, or isotopic compound thereof, wherein Z is selected from the group consisting of any of the following structures:

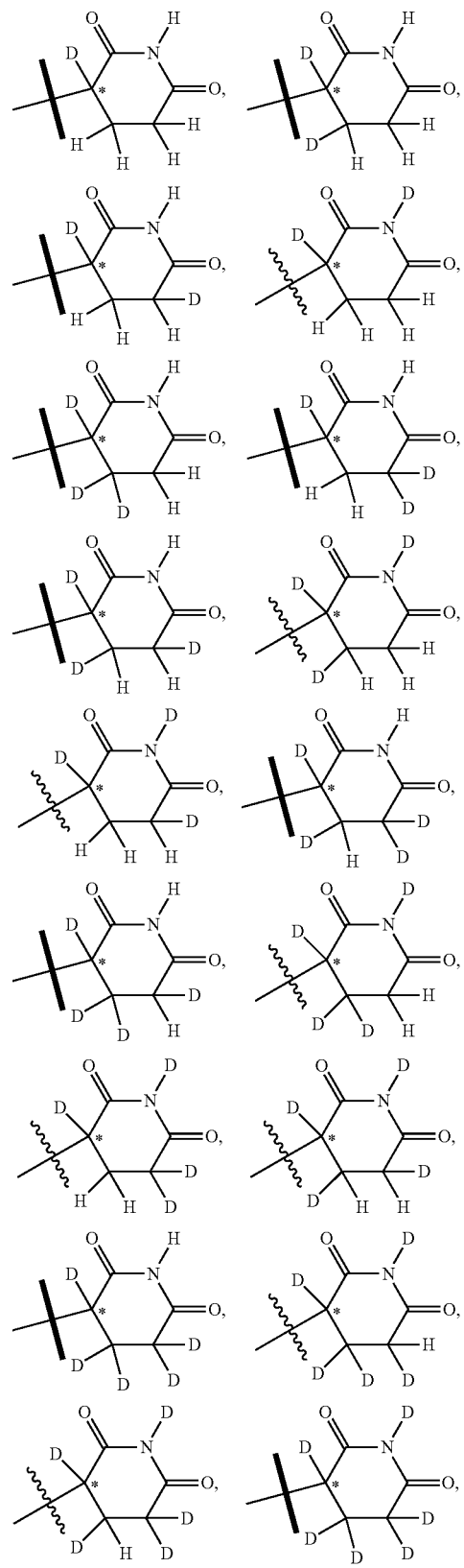

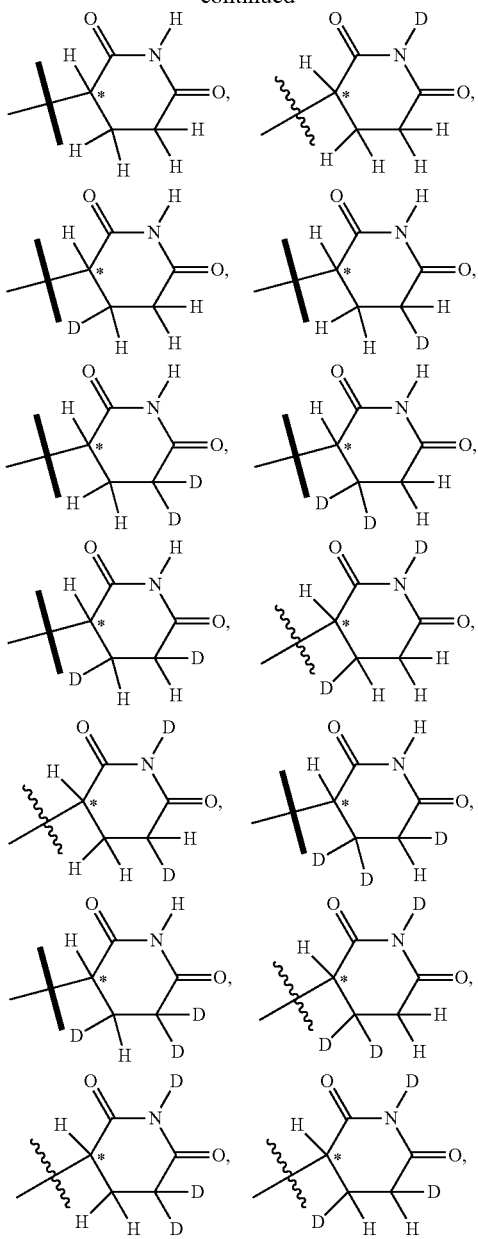

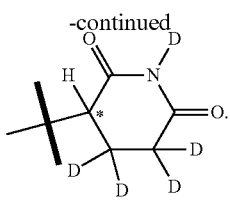

4. The compound of Formula I according to claim 1, or the pharmaceutically acceptable salt, solvate, stereoisomer, or isotopic compound thereof, wherein
R$^1$ is —NR$^{1'}$R$^{2'}$;
and/or R$^{y}$ and R$^{2'}$ are each independently selected from the group consisting of H, D, substituted or unsubstituted C$_1$-C$_4$ alkyl, and —C(O)R$^{3'}$; preferably R$^{y}$ and R$^{2'}$ are each independently selected from the group consisting of H, D, methyl, ethyl, isopropyl, acetyl, propionyl and isobutyryl;
and/or R$^{3'}$ is selected from the group consisting of substituted or unsubstituted C$_1$-C$_4$ alkyl.

5. The compound of Formula I according to claim 1, or the pharmaceutically acceptable salt, solvate, stereoisomer, or isotopic compound thereof, wherein
X is selected from the group consisting of halogen, hydroxyl, cyano, substituted or unsubstituted C$_1$-C$_4$ alkyl, and methoxy substituted with phenyl; wherein the phenyl is optionally substituted with one or more selected from the group consisting of D, halogen, hydroxyl, cyano, and C$_1$-C$_4$ alkyl substituted with morpholinyl, wherein when more than one substituents are present, they are identical or different.

6. The compound of Formula I according to claim 5, or the pharmaceutically acceptable salt, solvate, stereoisomer, or isotopic compound thereof, wherein
X is selected from the group consisting of fluorine, chlorine, bromine, hydroxyl, cyano, benzyloxy, 2-fluoro-4-(morpholinyl-1-methyl)benzyloxy, methyl, ethyl, CD$_3$, C$_2$D$_5$ and CH$_2$CD$_3$.

7. The compound of Formula I according to claim 1, or the pharmaceutically acceptable salt, solvate, stereoisomer, or isotopic compound thereof, wherein
X is halogen, le is NH$_2$, NHD or ND$_2$;
R$^2$, R$^3$, R$^5$, R$^6$, R$^7$, R$^8$, R$^9$ and R$^{10}$ are independently H or D;
R$^4$ is CH$_3$, CH$_2$D, CHD$_2$ or CD$_3$.

8. The compound of Formula I according to claim 1, or the pharmaceutically acceptable salt, solvate, stereoisomer, or isotopic compound thereof, wherein the compound of formula I is selected from any of the following structures:

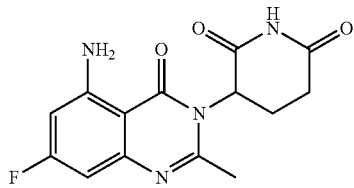

K101

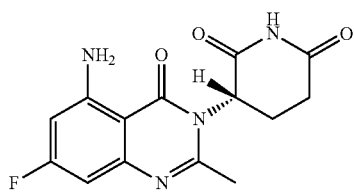

K102

-continued
K103
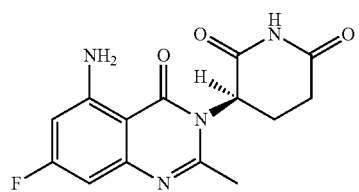
K104
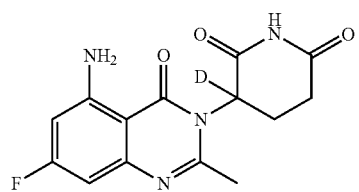
K105
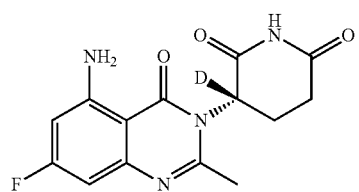
K106
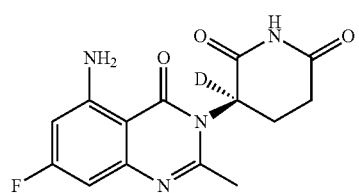
K113
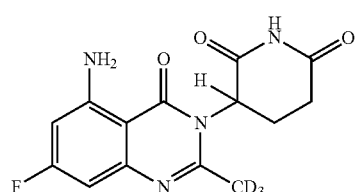
K116
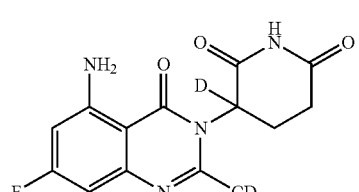
K113-1
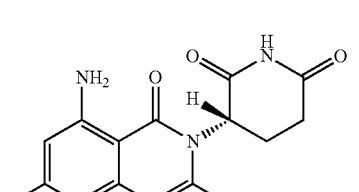
K118-1
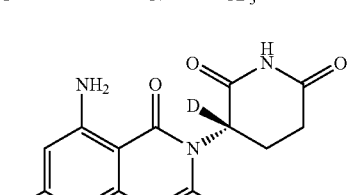
-continued
K401
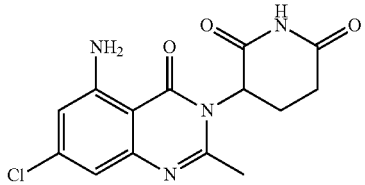
K402
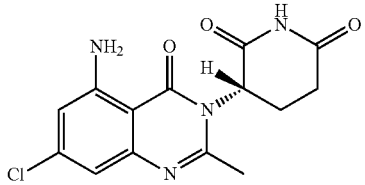
K403
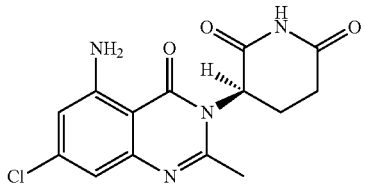
K404
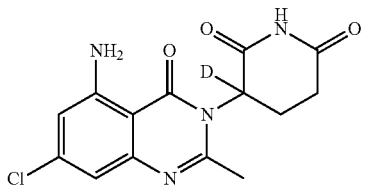
K405
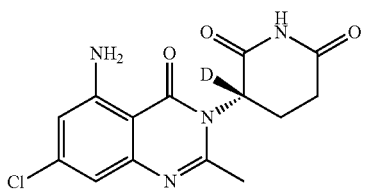
K406
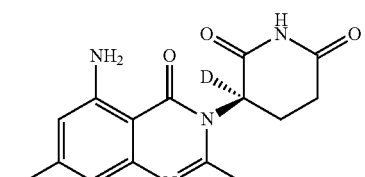
K409
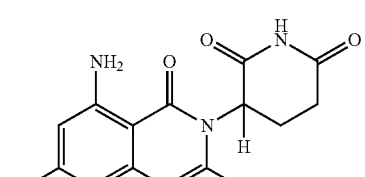
K409-1
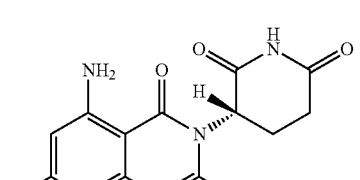

-continued
K410 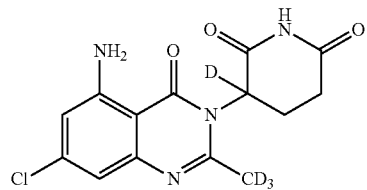
K410-1 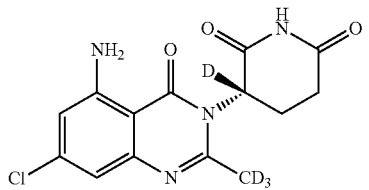
K431 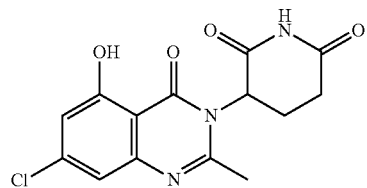
K431-1 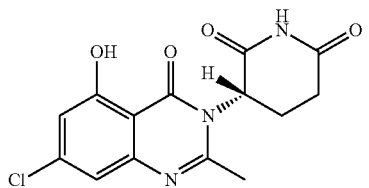
K432 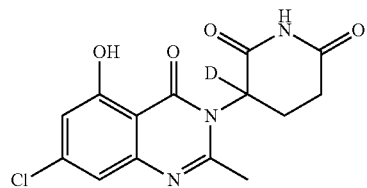
K432-1 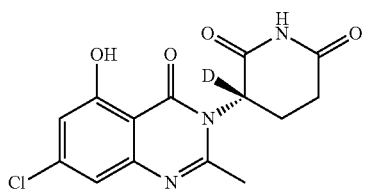
K501 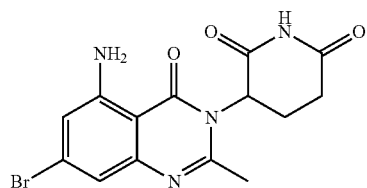
K502 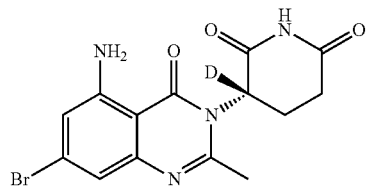
-continued
K503 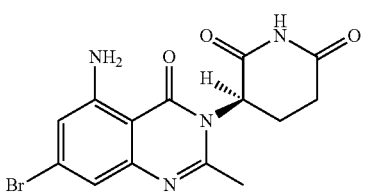
K504 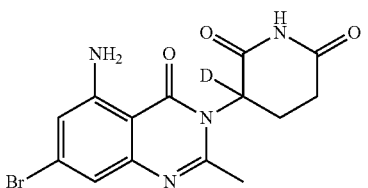
K505 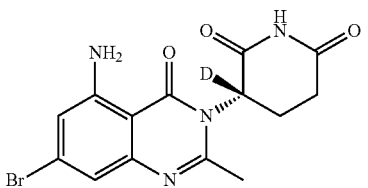
K506 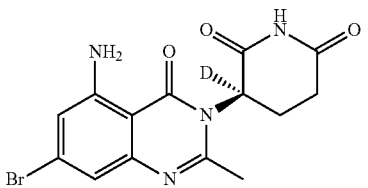
K509 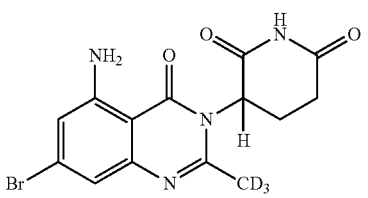
K509-1 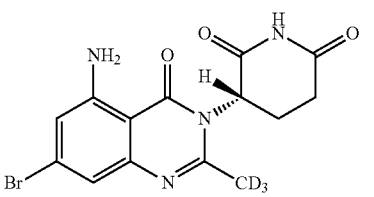
K510 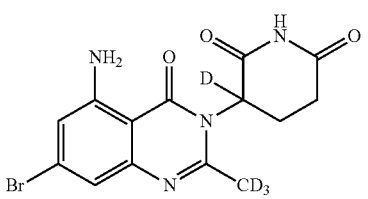
K510-1 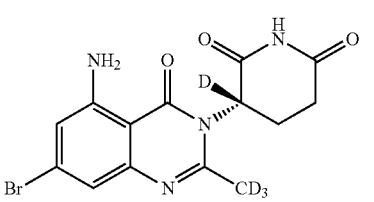

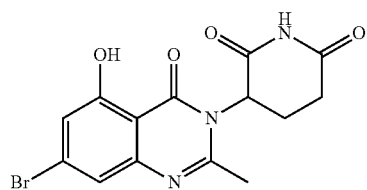
K531
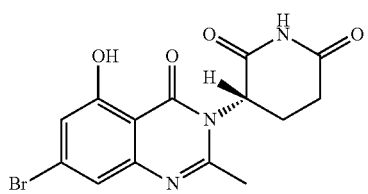
K531-1
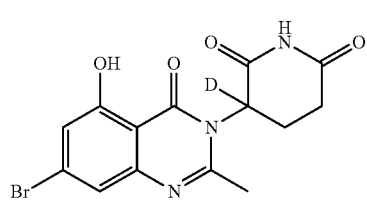
K532
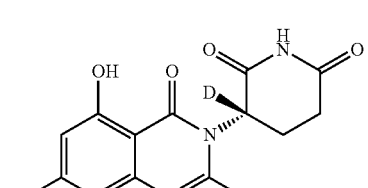
K532-1
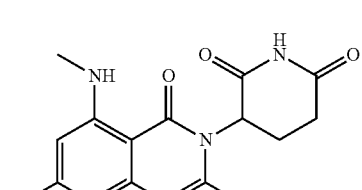
K613
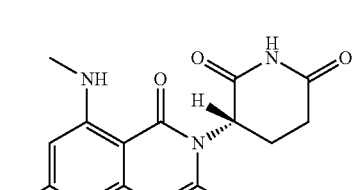
K613-1
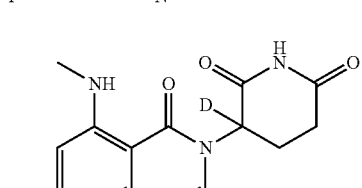
K614
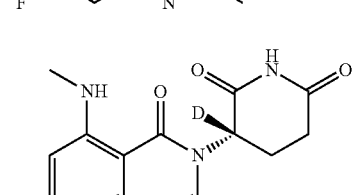
K614-1
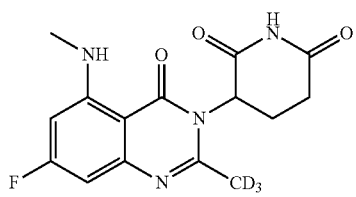
K615
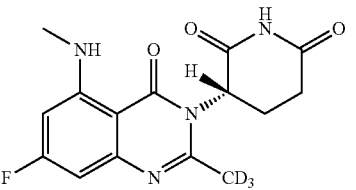
K615-1
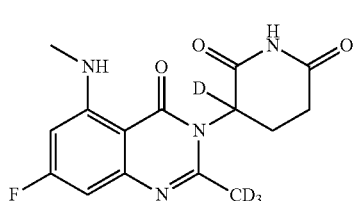
K616
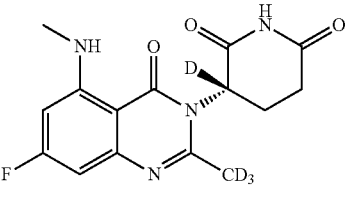
K615-1
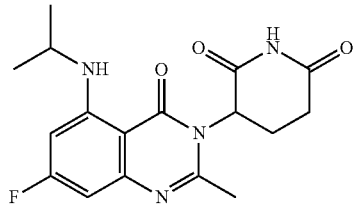
K617
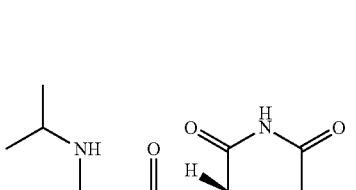
K617-1
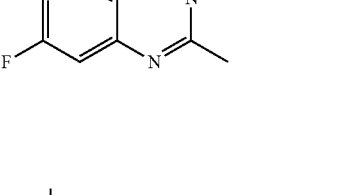
K620
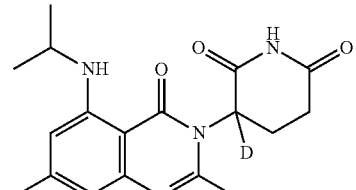

K620-1
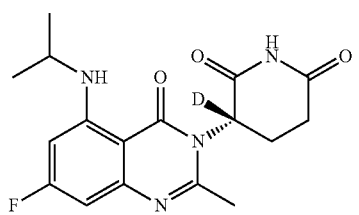
K627
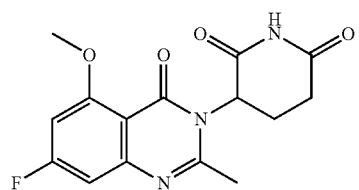
K627-1
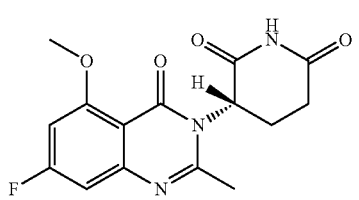
K628
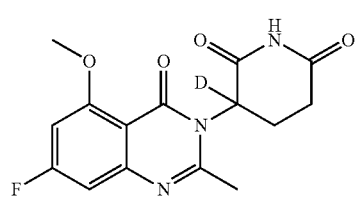
K628-1
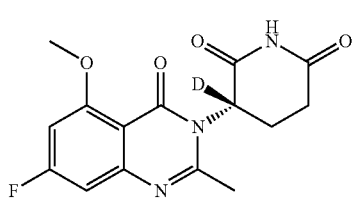
K631
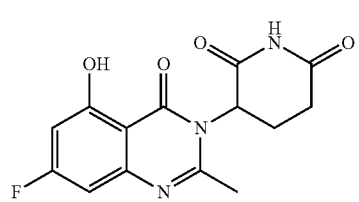
K631-1
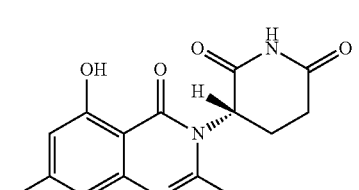
K632
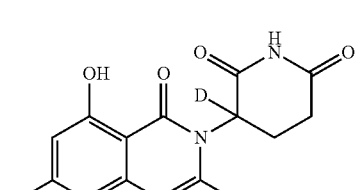
K632-1
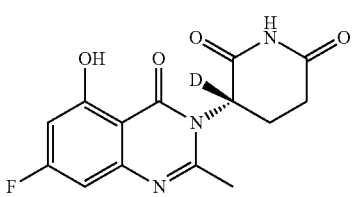
K633
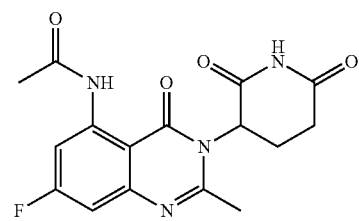
K633-1
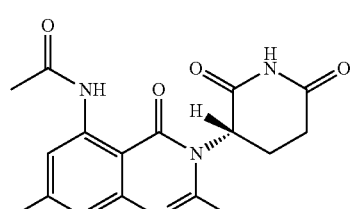
K634
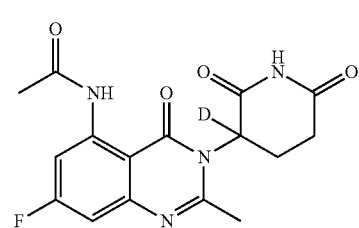
K634-1
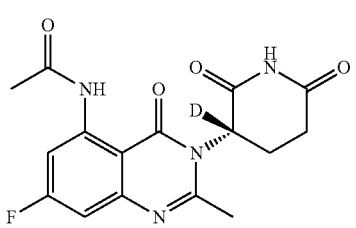
K635
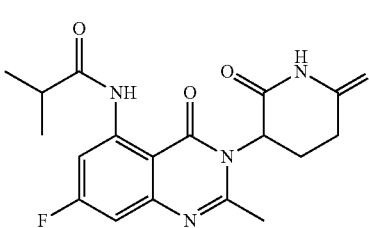
K635-1
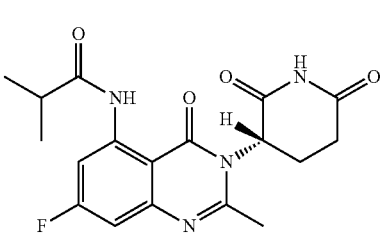

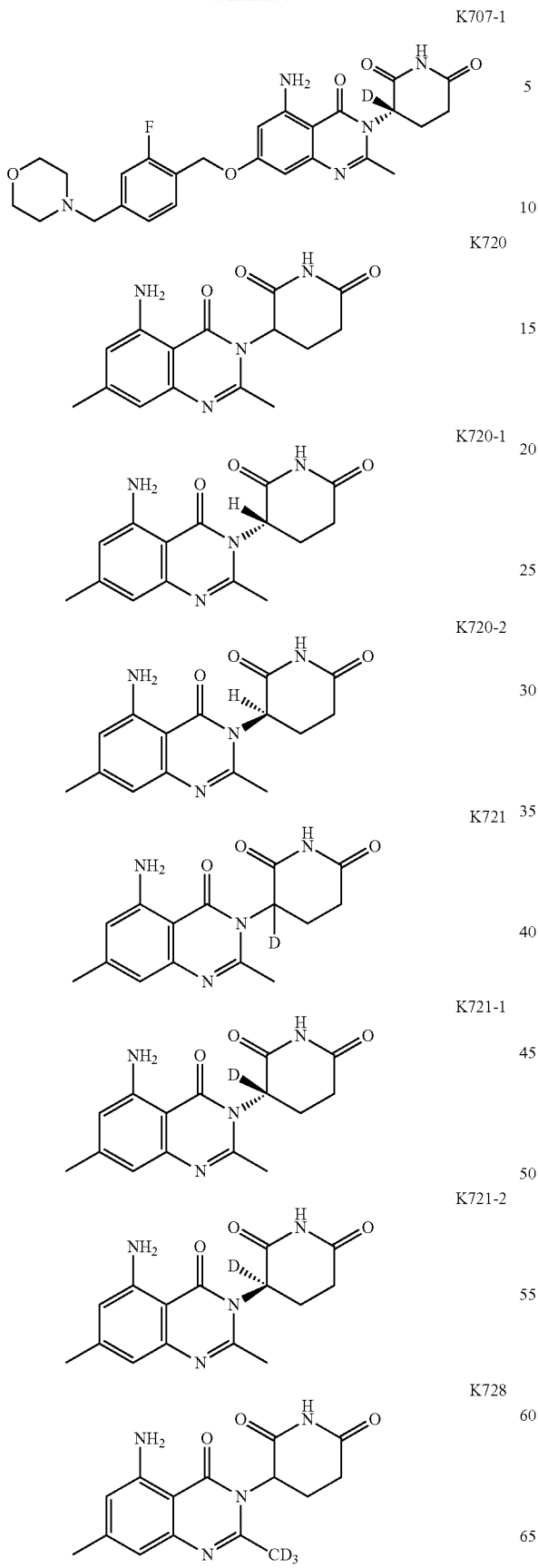
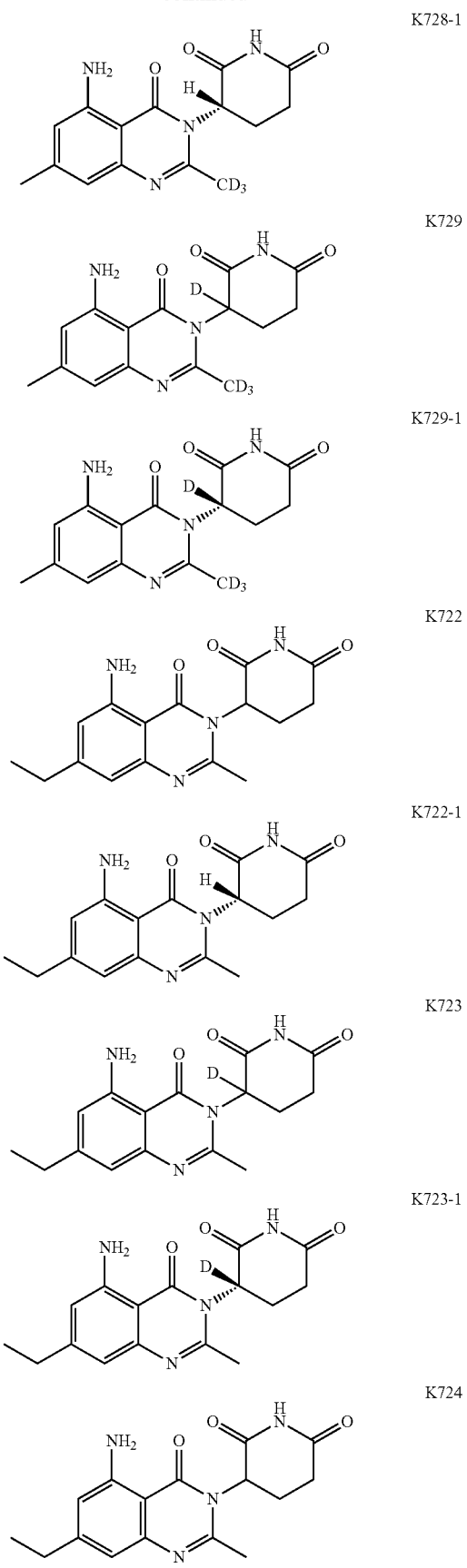

9. A process for preparing the compound of Formula I according to claim 1, or the pharmaceutically acceptable salt, solvate, stereoisomer, or isotopic compound thereof, which is selected from the group consisting of:

Process A comprising the following step:
reducing or deprotecting compound A1 to give the compound of Formula I wherein $R^{1a}$ is nitro, azide or $R^{1b'}$ and $R^{1b''}$ are independently H, D or amino protecting group, provided that $R^{1b'}$ and $R^{1b''}$ are not simultaneously H or D; and the definitions of $R^2$, $R^3$, $R^4$, X and Z are the same as for Formula I above.

10. The compound of Formula I according to claim 1, or the pharmaceutically acceptable salt, solvate, stereoisomer, or isotopic compound thereof, wherein
the 4-10 membered heterocycloalkyl is selected from the group consisting of pyrrolidinyl, piperidinyl, piperazinyl, and morpholinyl.

11. The compound of Formula I according to claim 1, or the pharmaceutically acceptable salt, solvate, stereoisomer, or isotopic compound thereof, wherein
Z is

[structures of Z shown]

12. The compound of Formula I according to claim 1, or the pharmaceutically acceptable salt, solvate, stereoisomer, or isotopic compound thereof, wherein
$R^1$ is —$NR^{1'}R^{2'}$;
and/or $R^{1'}$ and $R^{2'}$ are each independently selected from the group consisting of H, D, methyl, ethyl, isopropyl, acetyl, propionyl and isobutyryl.

13. The compound of Formula I according to claim 1, or the pharmaceutically acceptable salt, solvate, stereoisomer, or isotopic compound thereof, wherein
$R^1$ is —$NR^{1'}R^{2'}$;
and/or $R^{1'}$ and $R^{2'}$ are each independently selected from the group consisting of H, D, substituted or unsubstituted $C_1$-$C_4$ alkyl, and —$C(O)R^{3'}$;
and/or $R^{3'}$ is selected from the group consisting of methyl, ethyl and isopropyl.

14. A pharmaceutical composition comprising the compound of formula I according to claim 1, or the pharmaceutically acceptable salt, solvate, stereoisomer, or isotopic compound thereof, and one or more pharmaceutically acceptable excipients.

15. A process for preparing the compound of Formula I according to claim 1, or the pharmaceutically acceptable salt, solvate, stereoisomer, or isotopic compound thereof, which is selected from the group consisting of
Process B-1, comprising the following steps:
deprotecting compound B3 to give compound B2; and then subjecting compound B2 to amidation to give the compound of formula I;

[structure B3]

[structure B2]

[structure I]

Process B-2, comprising the following steps:
subjecting compound B3 to cyclization reaction to give the compound of formula I:

[structure B3]

[structure I]

wherein in Process B-1 and Process B-2, one of $R^a$ and $R^b$ is $-NR^{a'}R^{b''}$ and the other OH; is $-OtBu$, $-OBn$, or $-OMe$; one of $R^{a'}$ and $R^{b'}$ is $-NR^{a''}R^{b''}$, and the other is $-OH$; $R^{a''}$ and $R^{b''}$ are each independently H or D; and the definitions of $R^1$, $R^2$, $R^3$, $R^4$, $R^5$, $R^6$, $R^7$, $R^8$, $R^9$, X and Z are the same as for Formula I above.

16. A process for preparing the compound of Formula I according to claim 1, or the pharmaceutically acceptable salt, solvate, stereoisomer, or isotopic compound thereof, which is selected from the group consisting of
Process C-1, comprising the following steps:
reacting compound C1 and compound Z—$NH_2$ as shown below to give the compound of Formula I

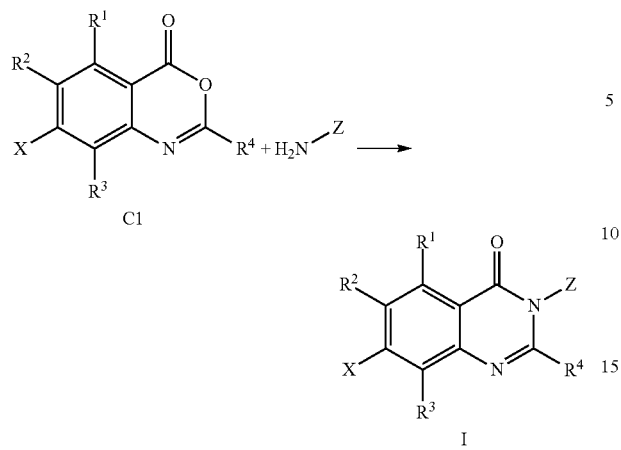

wherein the definitions of $R^1$, $R^2$, $R^3$, $R^4$, X and Z are the same as for Formula (I) above.

17. A method for regulating the generation or activity of TNF-α, comprising administering to a subject in need thereof a therapeutically effective amount of the compound of formula I according to claim 1, or the pharmaceutically acceptable salt, solvate, stereoisomer, or isotopic compound thereof.

* * * * *